US009809821B2

(12) United States Patent
Merzouki et al.

(10) Patent No.: US 9,809,821 B2
(45) Date of Patent: Nov. 7, 2017

(54) COMPOSITIONS AND METHODS FOR EFFICACIOUS AND SAFE DELIVERY OF SIRNA USING SPECIFIC CHITOSAN-BASED NANOCOMPLEXES

(71) Applicant: Polyvalor, Limited Partnership, Montreal (CA)

(72) Inventors: Abderrazzak Merzouki, Laval (CA); Michael D. Buschmann, Montreal (CA)

(73) Assignee: POLYVALOR, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 14/955,806

(22) Filed: Dec. 1, 2015

(65) Prior Publication Data

US 2016/0152988 A1    Jun. 2, 2016

Related U.S. Application Data

(63) Continuation of application No. 14/086,156, filed as application No. PCT/CA2012/050342 on May 24, 2012, now abandoned.

(60) Provisional application No. 61/489,306, filed on May 24, 2011, provisional application No. 61/489,302, filed on May 24, 2011.

(51) Int. Cl.
| | | |
|---|---|---|
| *A61K 48/00* | (2006.01) | |
| *C12N 15/113* | (2010.01) | |
| *A61K 38/00* | (2006.01) | |
| *A61K 38/28* | (2006.01) | |
| *A61K 45/06* | (2006.01) | |
| *A61K 9/51* | (2006.01) | |
| *A61K 31/40* | (2006.01) | |
| *A61K 31/403* | (2006.01) | |
| *A61K 31/4985* | (2006.01) | |
| *A61K 31/64* | (2006.01) | |
| *C12N 15/87* | (2006.01) | |
| *C12N 15/11* | (2006.01) | |
| *A61K 31/713* | (2006.01) | |
| *A61K 47/36* | (2006.01) | |

(52) U.S. Cl.
CPC ........ *C12N 15/1138* (2013.01); *A61K 9/5161* (2013.01); *A61K 31/40* (2013.01); *A61K 31/403* (2013.01); *A61K 31/4985* (2013.01); *A61K 31/64* (2013.01); *A61K 31/713* (2013.01); *A61K 38/005* (2013.01); *A61K 38/28* (2013.01); *A61K 45/06* (2013.01); *A61K 47/36* (2013.01); *C12N 15/111* (2013.01); *C12N 15/113* (2013.01); *C12N 15/1137* (2013.01); *C12N 15/87* (2013.01); *C12N 2310/14* (2013.01); *C12N 2310/531* (2013.01); *C12N 2320/31* (2013.01); *C12N 2320/32* (2013.01)

(58) Field of Classification Search
CPC ..................................................... A61K 48/00
See application file for complete search history.

(56) References Cited

U.S. PATENT DOCUMENTS

| | | | |
|---|---|---|---|
| 2002/0037836 A1* | 3/2002 | Henriksen .............. | A61K 38/26 514/11.7 |
| 2003/0171310 A1 | 9/2003 | Ward et al. | |
| 2005/0153914 A1 | 7/2005 | McSwiggen et al. | |
| 2007/0275914 A1* | 11/2007 | Manoharan ........ | A01K 67/0275 514/44 A |
| 2009/0215867 A1 | 8/2009 | Takagi et al. | |
| 2010/0015232 A1 | 1/2010 | Besenbacher et al. | |

FOREIGN PATENT DOCUMENTS

| | | |
|---|---|---|
| CA | 2644347 | 9/2007 |
| EP | 1816194 | 2/2009 |
| WO | 2006/054625 | 5/2006 |
| WO | 2007/059605 | 5/2007 |
| WO | 2008/020318 | 2/2008 |

OTHER PUBLICATIONS

Mao et al. (Advanced Drug Delivery Reviews 62 (2010) 12-27).*
Jean et al., "Chitosan-based therapeutic nanoparticles for combination gene therapy and gene silencing of in vitro cell lines relevant to type 2 diabetes", European Journal of Pharmaceutical Sciences, 45: 138-149 (2012).
Howard et al., "RNA Interference in Vitro and in Vivo Using a Chitosan/siRNA Nanoparticle System", Molecular Therapy, 14(4): 476-484 (2006).
Alameh et al., Int. J. Nanomedicine, 9(5): 473-481 (2010). "Chitosanase-based method for RNA isolation from cells transfected with chitosan/siRNA nanocomplexes for real-time RT-PCR in gene silencing."
Alameh et al., Int. J. Nanomedicine, 7: 1399-1414 (2012). "Low molecular weight chitosan nanoparticulate system at low N:P ratio for nontoxic polynucleotide delivery."
International Preliminary Report on Patentability issued on Nov. 26, 2013 in connection with PCT/CA2012050342, 8 pages.
International Search Report mailed on Jul. 31, 2012 in connection with PCT/CA2012/050342, 6 pages.
Salva et al., Oligonucleotides, 20(4): 183-190 (2010). "Chitosan/short hairpin RNA complexes for vascular endothelial growth factor suppression invasive breast carcinoma."

(Continued)

Primary Examiner — Kimberly Chong
(74) Attorney, Agent, or Firm — Nixon Peabody LLP; Elizabeth W. Baio; Nicole D. Kling

(57) ABSTRACT

There is disclosed a composition and a method for the efficient delivery of a therapeutic RNAi-inducing nucleic acid to cells both in vitro and in vivo through specific formulations of a non viral delivery system using chitosans. Particularly, the composition contains a nucleic acid and a specific chitosan that has the following physico-chemical properties: a number-average molecular weight between 5 kDa and 200 kDa, a degree of deacetylation between 80% and 95% and a chitosan amine to nucleic acid phosphate ratio below 20.

24 Claims, 18 Drawing Sheets

(56) References Cited

OTHER PUBLICATIONS

Supplemental European Search Report issued on Oct. 27, 2014 in connection with EP application 12788754.5, 9 pages.
Written Opinion of the International Searching Authority issued on Jul. 31, 2012 in connection with PCT/CA2012/050342, 7 pages.
Wang et al., "Recent advances of chitosan nanoparticles as drug carriers", International Journal of Nanomedicine, 6: 765-774 (2011).
Futami et al. "Anticancer activity of RecQL1 helicase siRNA in mouse xenograft models." Cancer Science 99 (6):1227-1236 (2008).
Laveru et al. "High efficiency gene transfer using chitosan/DNA nanoparticles with specific combinations of molecular weight and degree of deacetylation." Biomaterials 27(27):4815-4824 (2006).
Zimmermann et al. "RNAi-mediated gene silencing in non-human primates." Nature 441(7089):111-114 (2006).

\* cited by examiner

COMPOSITIONS AND METHODS FOR EFFICACIOUS AND SAFE DELIVERY OF SIRNA USING SPECIFIC CHITOSAN-BASED NANOCOMPLEXES

CROSS-REFERENCE TO RELATED APPLICATIONS

This application is a continuation application of U.S. application Ser. No. 14/086,186, filed on Nov. 21, 2013, which is a 35 U.S.C. §371 national phase entry Application of International Application No. PCT/CA2012/050342 filed May 24, 2012, which designates the U.S., and which claims benefit under 35 U.S.C. §119(e) of U.S. Provisional Application Nos. 61/489,306 and 61/489,302 filed May 24, 2011, the contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Dec. 8, 2014, is named 030841-082170_SL and is 3,534 bytes in size.

TECHNICAL FIELD

The present description relates to a composition and a method for the efficient delivery of a therapeutic RNAi-inducing nucleic acid using specific chitosan based nanocomplexes.

BACKGROUND

Gene silencing by siRNA (short interfering RNA) is a developing field in biology and has evolved as a novel post-transcriptional gene silencing strategy with therapeutic potential. Based on the sequencing of the human genome and the understanding of the molecular causes of diseases, the possibility of turning off pathogenic genes at will is an appealing approach for treatment of a wide variety of clinical pathologies, such as diabetes, atherosclerosis and cancer. With siRNAs, virtually every gene in the human genome contributing to a disease becomes amenable to regulation, thus opening opportunities for drug discovery. Whereas locally administered siRNAs have already entered the first clinical trials, strategies for successful systemic delivery of siRNA are still in a preclinical stage of development.

Type II Diabetes Mellitus

Type II diabetes mellitus (T2DM) is a progressive metabolic disorder with diverse pathologic manifestations and is often associated with lipid metabolism and glycometabolic disorders (Bell et al., 2001, Nature, 414:788-791). Type II diabetes is characterized by a resistance to insulin action in peripheral tissues such as muscle, adipose tissue and liver. It is also characterized by a progressive failure in the ability of the islet β-cell to secrete insulin. The long term effects of diabetes result from its vascular complications; micro vascular complications, retinopathy, neuropathy and nephropathy. Macro vascular complications are associated with type II diabetes as well, and include cardiovascular and cerebrovascular complications.

The main classes of anti-diabetic drugs known today are the following. Biguanides are a class of drugs that help control blood glucose by inhibiting hepatic glucose production, reducing intestinal absorption and enhancing peripheral glucose uptake. This class includes metformin, a drug that lowers both glucose and blood triglycerides level. Sulfonylurea is a class of drugs that helps in controlling or managing type II diabetes by stimulating the release of endogenous insulin from the β-cells of the pancreas. This class includes: tolbutamide, tolazamide, glisoxepide, glimipeide and glibomuride among others. Glycosidase inhibitors stimulate the release of insulin from pancreatic cells thus lowering blood sugar level and include repaglinide and nateglinide.

Unfortunately, these treatment modalities, even when combined, are frequently constrained by safety, tolerability, weight gain, oedema and gastrointestinal intolerance (Drucker et al., 2010, Nat Rev Drug Discov, 9:267-268; Nauck et al., 2009, Diabetes Care, 32:84-90; Ng et al., 2010, Prim Care Diabetes, 4:61-63; Truitt et al., 2010, Curr Med Res Opin, 26:1321-1331; and Wajcberg and Tavaria, 2009, Expert Opin Pharmacother, 10:135-142). In addition, as the disease progresses and β-cell function declines, efficacies of current treatments diminish (Turner et al., 1999, JAMA, 281:2005-2012).

The discovery of the incretin effect has provided a new avenue of treatment using a class of therapeutics capable of controlling T2DM with minimal adverse effects. The incretin effect is mainly mediated by glucagon like peptide 1 (GLP-1) which regulates postprandial blood glucose level via the stimulation of insulin secretion. GLP-1 has also indirect effects such as delay of gastric emptying, promoting satiety through its effect on the central nervous system, promoting β-cell growth and inhibiting β-cell apoptosis as demonstrated in animal models (Nauck et al., 2002, J Clin Endocrinol Metab, 87:1239-1246; and Creutzfeldt et al., 1996, Diabetes Care, 19:580-586). However, the potential of GLP-1 in the clinic was hindered due to its rapid degradation by the ubiquitous serine protease dipeptidyl peptidase IV (DPP-IV). The discovery that DPP-IV cleaves the His:Ala: Glu sequence at the N-terminal region of GLP-1 permitted the development of DPP-IV resistant GLP-1 analogues and the development of DPP-IV inhibitors.

DPP-IV inhibitors are a new class of drugs that inhibit the proteolytic activity of dipeptidyl peptidase IV. The proteolytic activity of DPP-IV decreases blood level of glucoregulatory peptides, known as incretins. Inhibition of dipeptidyl peptidase IV thereby potentiates the action of these incretin, notably glucagon like peptide 1 (GLP-1). These inhibitors include Sitagliptin, Vildagliptin and Saxagliptin and are orally administrated once daily.

Atherosclerosis

Atherosclerosis is a chronic disease caused by the formation of atherosclerotic plaque in arteries. Atherosclerosis represents a multitude of cardiovascular diseases such as coronary heart disease, acute coronary syndrome and angina pectoris (Lloyd-Jones et al., 2010, Circulation, 121:e46-e215). In the United-States, the predicted economic cost of atherosclerosis for 2010 was US$503 billion, mainly due to direct medical and indirect productivity costs (Lloyd-Jones et al., 2010, Circulation, 121:948-954). Although causal factors for atherosclerosis remain unknown, increasing evidence suggest a high role of dyslipidemia, hyperlipidemia and inflammation in the pathogenesis of this disease (Hanson et al., 2006, Nat Rev Immunol, 6:508-519; Montecucco and Mach, 2008, Clin Intery Aging, 3:341-349). Currently, the reduction of morbidity and mortality due to atherosclerosis and related pathologies—Cardiovascular Diseases (CVD)—are mainly attributable to the aggressive clinical use of 3-hydroxy-3-methylglutaryl coenzyme A (HMG-CoA) reducatase inhibitors commonly named statin-based therapies (Vermissen et al., 2008, BMJ, 337:a2423). These therapies reduce low density lipoprotein cholesterol (LDL-C). Intervention studies have demonstrated reduced risk of CVD morbidity and mortality when lipid lowering therapies were administered. Additionally, the decreased morbidity/mortality and LDL-C lowering demonstrate a log-linear association (Law et al., 1994, BMJ, 308:367-372).

An alternative approach to lowering LDL-C, and thus reducing atherosclerosis, is the inhibition or blocking of very low density lipoprotein (VLDL) secretion from the liver. This inhibition can be achieved through apolipoprotein B (ApoB) targeting since ApoB is necessary for VLDL secretion (Rutledge et al., 2010, Cell Biol, 88:251-267). ApoB is mainly expressed by hepatocytes and entherocytes in humans.

In humans, the ApoB gene is located on chromosome 2 (2q) and spans over 43 kb. ApoB mRNA consists of 28 introns and 29 exons and is characterized by a 16 hour half life (Ludwig et al., 1987, DNA, 6:363-372; Scott, 1989, Curr Opin Cell Biol, 1:1141-1147). The translation of ApoB mRNA yields a protein with 4,536 amino acids and an apparent molecular weight of 517-550 kDa thus representing one of the largest monomeric proteins. The importance of ApoB inhibition as an alternative therapy for atherosclerosis and its associated CVDs resides in the ability of ApoB to physically interact through its β-sheet domains with lipids such as phospholipids, cholesterol and cholesteryl esters to form large lipoproteins particles, namely VLDL, in the liver and cholymicrons in the intestine (reviewed in Rutledge et al., 2010, Biochem Cell Biol, 88:251-267).

Cancer

Classical cancer therapy includes the use of one or several chemotherapeutic drugs. These treatment modalities are associated with toxicity and severe side effects due to their non-specificity. Another major problem associated with chemotherapy is the development of chemoresistance with time. For example, resistance to chemotherapy is one of the major problems associated with the management of breast cancer.

Cancer cells employ a plethora of mechanisms to acquire resistance to one or more chemotherapeutic agent. Major mechanisms of drug resistance include (1) decreased intracellular uptake of soluble drugs, (2) genetic and phenotypic changes in cells that change the capacity of drugs to cause the desired cell damage and (3) increased efflux of drugs by cell-surface transporters, leading to multidrug resistance (MDR). In all these cases resistance to a single chemotherapeutic entity is always associated with a wide-range drug resistance pattern against other chemotherapeutics.

One of the most common and studied resistance mechanisms is the reduction of intracellular drug concentration by transporter proteins that pump drugs out of cells before they reach the site of action, so that the cells adapt to low drug concentration without undergoing drug-induced cell death. Most of these transporters are in the ATP-binding cassette transmembrane protein super-family.

In humans, 48 ABC genes (genes in the ATP-binding cassette family) have been identified to date. In breast cancer, practically all MDR resistance reported to date were closely related to one of the following: p-glycoprotein (P-gp), multidrug resistance-related protein (MRP), and breast cancer resistance protein (BCRP).

The P-gp is the most common protein involved in ATP-dependent efflux of drugs in various cancer tissues. The over expression P-gp was believed for some time to be the only protein capable of conferring MDR in mammalian tumor cells. In breast cancer, 52% of chemotherapy-treated patients had their P-gp up regulated due to therapy. The gene encoding P-gp is termed ABCB1 (mdr1) and is located on chromosome 7 at the position q21.12. ABCB1 is composed of 28 exons whose product yield a 1.2 kb mRNA. Protein sequence analysis of P-gp revealed the presence of 2 extracytoplasmic domains, each containing 6 putative transmembrane segments, and an ATP-binding consensus motif.

Furthermore, one class of interesting enzymes involved in maintenance of genomic integrity and stability are DNA helicases. These proteins play important roles in DNA replication, repair, recombination and transcription by an ATP dependant mechanism that unwinds duplex genomic strands allowing the repair machinery access to damaged or mispaired DNA.

For example, the RecQ family of helicases has been shown to play an important role in recombination, repair and Holliday junction formation. More recently, these helicases have been implicated in the process of posttranscriptional gene silencing (Cogoni and Macino, 1999, Science, 286: 2342-2344). In this process, the helicase is required to separate the double stranded DNA before any hybridization and silencing mechanism could be initiated. Other roles have been put forward for proteins of this family. For example, RecQL1 is believed to play a role in nuclear protein transport since it interacts with both QIP1 and QIP2 proteins which function as nuclear localization signals as demonstrated in a two hybrid screening (Seki et al., 1997, 234:48-53).

The RecQ family consists of five members and can be divided into two groups according to whether they contain an additional carboxy- or amino-terminus group. Mutations in these genes lead to increased incidence of cancer as well as other physiologic abnormalities (Karow et al., 2000, Curr Opin Genet Dev, 10:32-38; Kawabe et al., 2000, Oncogene, 19:4767-4772). Such abnormalities include Blooms syndrome (BLM), Wemer's syndrome (WRN) and the Rothmund-Thompson syndrome (RecQ4). The human RecQL1 gene was the first human member of this family to be identified and was shown to have extensive homology with the *E.coli* DNA helicase, RecQ, and is located on chromosome 12p11 (Puranam and Blackshear, 1994, J Biol Chem, 269:29838-29845; Puranam et al., 1995, Genomics, 26:595-598).

RecQL1 over expression in cancerous cell lines such as AsPC1, A549 and LS174T among others is believed to be driven in order to compensate the high recombination rate in these cancerous cells, thus preventing apoptosis (Futami et al., 2008, Cancer Sci, 99:71-80). RecQL1 gene silencing using specific siRNA in these cell lines or in a murine Xenograft model lead to an increased cancerous cell death and tumor mass reduction (Futami et al., 2008, Cancer Sci, 99:71-80).

Another class of enzymes involved in maintenance of homeostatic stability and functional integrity are RNA helicases. These enzymes are characterized by the presence of a centrally located "helicase domain", consisting of eight conserved motifs. Based on these motifs, RNA helicases are classified into families. These conserved motifs are required to perform the NTP hydrolysis and RNA unwinding functions (Linder et al., 2001, Trends Biochem Sci., 26:339-341; Tanner and Linder, 2001, Mol Cell, 8:251-262). Another function that has been associated with RNA helicases is disruption of RNA-protein interactions (Jankowsky et al., 2001, Science, 291:121-125). These enzymes are members of molecular complexes that can regulate both their NTPase and helicase activities (Silverman et al., 2003, Gene, 312: 1-16). The intrinsic characteristics of these helicases play an important role in post transcriptional events since the modulation of RNA secondary structure regulates steps such as splicing (Balvay et al., 1993, Bioessays, 15:165-169) and translation (van der Velden and Thomas, 1999, Int J Biochem Cell Biol, 31:87-106).

Dysregulation of RNA processing molecules such as RNA helicase have been implicated in human pathologies and cancer development. Examples of these helicases implicated in human pathologies include DDX1/5/6/9/10 and DHX32 among others (Abdelhaleem, 2004, Anticancer Res, 2004, 24:3951-3953; Abdelhaleem, 2004, Biocim Biophys Acta, 1704:37-46). These helicases contain a characteristic DEAD box domain and are up-regulated in most cancers (Abdelhaleem, 2004, Anticancer Res, 2004, 24:3951-3953; Abdelhaleem, 2004, Biocim Biophys Acta, 1704:37-46).

There is still a need today to be provided with alternative therapies by sustaining siRNA delivery in vivo. Particularly, it would be highly desirable to be provided with an alternative means for treating type II diabetes mellitus, atherosclerosis and cancer.

SUMMARY

One aim of the present description is to provide a composition comprising chitosan and an RNA-inducing nucleic acid sequence wherein the chitosan has a molecular weight (Mn) of 5 kDa to 200 kDa, a degree of deacetylation (DDA) of 80% to 95%, and wherein the chitosan amine to nucleic acid phosphate ratio (N:P) is below 20.

Another aim of the present description is to provide a composition as described herein for the treatment of diabetes mellitus, atherosclerosis or cancer and/or related conditions in a patient.

In accordance with the present description there is provided a method of producing a composition for treating diabetes mellitus, atherosclerosis or cancer and/or related conditions comprising admixing chitosan and an RNA-inducing nucleic acid sequence in an acidic medium, wherein the chitosan has a molecular weight (Mn) of 5 kDa to 200 kDa, a degree of deacetylation (DDA) of 80% to 95%, and wherein the chitosan amine to nucleic acid phosphate ratio (N:P) is below 20.

In accordance with the present description, it is also provided the use of a composition as defined herein for the treatment of diabetes mellitus, atherosclerosis or cancer and/or related conditions in a patient; or in the manufacture of a medicament for the treatment of diabetes mellitus, atherosclerosis or cancer and/or related conditions in a patient.

One aim of the present description is to provide a composition as described herein for the treatment of cancer in a patient or the reversal of chemoresistance or a combination of both. In accordance with the present description there is provided a method of producing a composition for treating cancer or sensitizing chemoresistant cancer to classical chemotherapy or both.

Another aim of the present description is to provide a method of treating diabetes mellitus, atherosclerosis or cancer and/or related conditions in a patient comprising administering to the patient an effective amount of a composition as defined herein, more particularly a composition comprising chitosan and an RNA-inducing nucleic acid sequence, wherein the chitosan has a molecular weight (Mn) of 5 kDa to 200 kDa, a degree of deacetylation (DDA) of 80% to 95%, and wherein the chitosan amine to nucleic acid phosphate ratio (N:P) is below 20.

It is also provided a method for delivering a nucleic acid sequence into a cell comprising the step of contacting the composition as described herein with the cell.

In an embodiment, the molecular weight of chitosan is 5 to 15 kDa, the DDA from 90 to 95% and the N:P ratio is from 2 to 10; preferably the molecular weight of chitosan is 10 kDa, the DDA is 92% and the N:P ratio is 5.

In a further embodiment, the molecular weight of chitosan is 10 kDa, 40 kDa, 80 kDa, 150 kDa or 200 kDa.

In another embodiment, the chitosan comprises block distribution of acetyl groups or a chemical modification.

In a further embodiment, chitosan has a polydispersity between 1.0 and 7.0.

In a further embodiment, the RNA-inducing nucleic acid sequence is a double stranded linear deoxyribonucleic acid sequence between 10 to 50 nucleotides; the RNA-inducing nucleic acid sequence is a double stranded linear ribonucleic acid sequence between 10 to 50 nucleotides; the RNA-inducing nucleic acid sequence is a hairpin structure of deoxyribonucleic or ribonucleic acid sequence; and/or the RNA-inducing nucleic acid sequence is a short interfering RNA, a short hairpin RNA or an RNAi-inducing vector.

In another embodiment, the RNAi-inducing nucleic acid sequence is chemically modified either on the sugar backbone, phosphate backbone and/or the nucleotide base ring.

Preferably, the RNA-inducing nucleic acid sequence targets a gene involved in the pathogenesis of type II diabetes, atherosclerosis or cancer; such as for example a gene involved in tumor development, metastasis or the induction or acquisition of chemoresistance, a glycoregulating protein or an atherogenic protein; such as for example an incretin degrading enzyme; such as for example dipeptydilpeptidase-IV (DPP-IV); such as for example Apolipoprotein B (ApoB), Apolipoprotein E (ApoE), Apolipoprotein B 100 (ApoB 100), Apolipoprotein B 48 (ApoB 48), Neutrophil gelatinase-associated lipocalin (NGAL), Matrix metalloproteinase-9 (MMP-9), or Cholesteryl ester transfer protein (CETP).

In another embodiment, the RNAi-inducing nucleic acid sequence targets a helicase protein, an RNA helicase, P68, DDX5, DDX32, DDX1, Akt, PKB, a member of the ABC transporters, MDR1, MRP, a member of the RAS family of proteins, SRC, HER2, EGFR, Abl, or Raf.

In another emdobiment, the helicase protein is a member of the RecQ family of helicases, such as for example RecQL1 DNA helicase. Additionally, the RNAi-inducing nucleic acid sequence targets MDR1.

In another embodiment, the diabetes mellitus related conditions are insulin-dependent diabetes mellitus (type I diabetes), noninsulin-dependent diabetes mellitus (type II diabetes), insulin resistance, hyperinsulinemia, diabetes-induced hypertension, obesity, damage to blood vessels, damage to eyes, damage to kidneys, damage to nerves, damage to autonomic nervous system, damage to skin, damage to connective tissue, and damage to immune system.

In a further embodiment, the atherosclerosis related conditions are cardiovascular diseases, such as for example coronary heart diseases, acute coronary syndromes or angina pectori.

In another embodiment, the composition reduces ApoB plasma levels; increases GLP-1 bioavailability; increases the control of glucose metabolism in the patient; reduces the blood glucose level in the patient; reduces the cholesterol level in the patient; reduces the low-density lipoprotein level in the patient; and/or reduces the weight gain in the patient.

In a further embodiment, the composition reduces ApoB plasma levels of at least 35% and LDL/VLDL cholesterol level of at least 20%.

In another embodiment, the composition is formulated for a subcutaneous administration, an intramuscular administration, an intravenous administration, an intradermal administration, intramammary administration, an intraperitoneal administration, an oral administration or a gastrointestinal administration.

In a particular embodiment, the composition is formulated for an injection at a dose of 1 mg/kg.

In another embodiment, the composition described herein can comprise insulin, a glucosidase inhibitor, a sulfonylurea, a DPP-IV inhibitor or a hypoglycemic compound.

The composition described herein can also be formulated for concurrent administration with a suitable delivery reagent, insulin or a hypoglycemic compound; such as a delivery agent being Mirus Transit TKO® lipophilic reagent, Lipofectin®, Iipofectamine™, Cellfectin®, polycations or liposomes; or such as an hypoglycemic compound being metformin, acarbose, acetohexamide, glimepiride, tolazamide, glipizide, glyburide, tolbutamide, chlorpropamide, thiazolidinediones, alpha glucosidase inhibitors, biguanindine derivatives, troglitazone, or a mixture thereof; such an sulfonylurea being tolbutanide, tolazamide, glisoxepide, glimipeide or glibomuride; such as a DPP-IV inhibitor being sitagliptin, vildagliptin or saxagliptin.

In an embodiment, the cancer is breast cancer, glioma, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, Hodgkin's disease, non-Hodgkin's lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma, testicular cancer, oral cancer, pharyngeal cancer, pediatric neoplasms, leukemia, neuroblastoma, retinoblastoma, glioma, rhabdomyoblastoma or sarcoma.

In another embodiment, the composition is formulated for concurrent administration with at least one of a suitable delivery reagent and an anti-cancer compound.

The suitable delivery agent can be Mirus Transit TKO® lipophilic reagent, Lipofectin®, Lipofectamine™, Cellfectin®, polycations or liposomes.

It is also described that the composition is formulated for concurrent administration during a suitable anti-cancer therapy, such as an anti-cancer therapy being at least one of a surgical procedure, chemotherapy, hormonal therapy and localization radiation.

In a preferred embodiment, the composition does not induce liver toxicity and inflammation when administered.

The composition described herein can further comprise a transfection media having a pH varying from 5 to 7.1; can be formulated as a dried powder, and/or is a particulate suspension in aqueous media.

In another embodiment, the chitosan is dissolved in hydrochloric acid prior to admixing with the RNA-inducing nucleic acid sequence.

Preferably, the chitosan is dissolved in a glucosamine:HCl at a ratio of 1:1.

In another embodiment, the admixing of chitosan with the RNA-inducing nucleic acid sequence produces nanoparticles of spherical shape of sizes below 200 nm, preferably the size of 45 to 156 nm.

In an embodiment, the cell is a primary cell, a transformed cell or an immortalized cell.

In another embodiment, the chitosan is dissolved in hydrochloric acid prior to admixing with the RNAi-inducing nucleic acid sequence.

In another embodiment, the Mn of chitosan is 10 kDa, the DDA is of 80% or 92%, and wherein the chitosan amine to nucleic acid phosphate ratio (N:P) is of 5 or 10.

BRIEF DESCRIPTION OF THE DRAWINGS

Reference will now be made to the accompanying drawings.

DETAILED DESCRIPTION

Figure 1A:
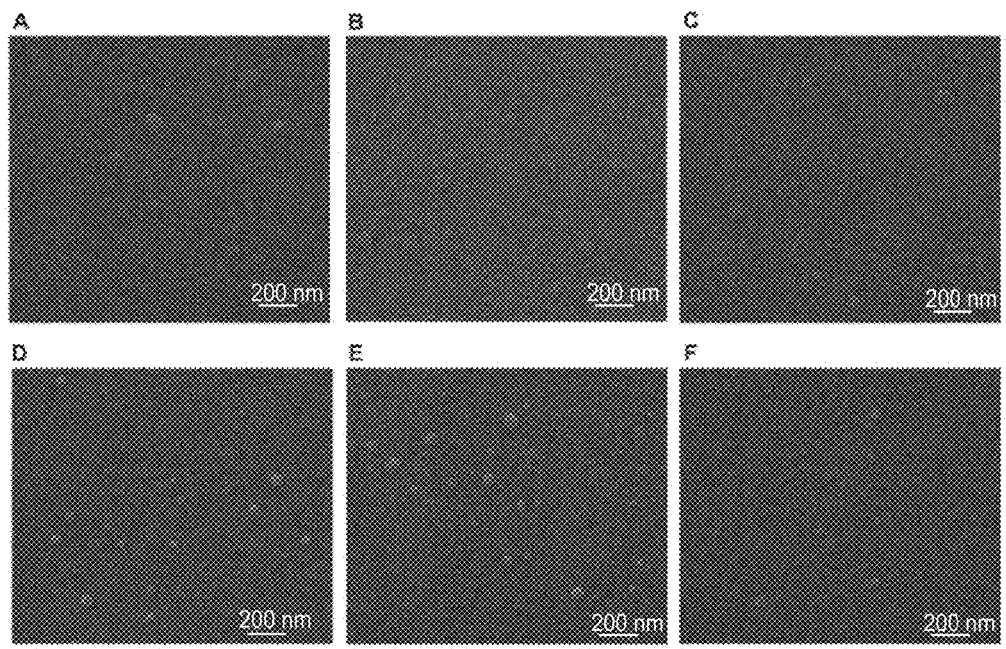
FIG. 1A illustrates environmental scanning electron microscopy (ESEM) images of spherical chitosan/dsODN nanoparticles and population size distribution of (A) 92-10-5 chitosan/dsODN-DPP-IV nanoparticles, (B) 80-80-5 chitosan/dsODN-DPP-IV nanoparticles, (C) 80-10-10 chitosan/dsODN-DPP-IV nanoparticles, (D) 92-10-5 chitosan/dsODN-ApoB nanoparticles, (E) 80-80-5 chitosan/dsODN-ApoB nanoparticles and (F) 80-10-10 chitosan/dsODN-ApoB nanoparticles.

In accordance with the present disclosure, there is provided a novel and specific composition of a non viral vector for the efficient delivery of RNAi inducing entities such as short interfering RNAs (siRNAs), short hairpin RNAs (shRNAs), and RNAi-inducing vectors (i.e., vectors whose presence within a cell results in production of a siRNA or shRNA) to cells, tissues and organs in mammals, e.g., human. In particular, the description provides chitosan compositions with specific average molecular weight (Mn) and degree of deacetylation (DDA) ranges comprising RNAi inducing entities with specific chitosan to nucleic acid ratios.

There is thus provided compositions and methods of treating or preventing diseases or conditions associated with excessive expression or inappropriate expression of a target transcript; or inappropriate or excessive activity of a polypeptide encoded by the target transcript.

The compositions provided herein can be used in order to provide symptomatic relief, by administering RNAi inducing entities using the compositions disclosed herein to a subject at risk of, or, suffering from such a condition within an appropriate time window prior to, during, or after the onset of symptoms.

The compositions and methods may be applied for a variety of purposes, such as for example, but not limited to, studying the function of the transcript, studying the effect of different compounds of a cell or organism in the absence of, or with reduced activity of, the polypeptide encoded by the transcript. Furthermore, the composition and methods may be applied in clinical therapy for type II diabetes and its related pathologies, atherosclerosis and its related pathologies and cancer. Specifically, the compositions and methods may be applied for the inhibition of incretin degrading enzymes (DPP-IV) or any glycoregulating protein in order to treat diabetes, applied for the inhibition of ApoB gene or any atherogenic protein (i.e ApoE) in order to treat atherosclerosis, or for down-regulating the expression of RecQL1 DNA helicase or DDX5-p68-RNA helicase respectively, but not limited to those, for treating cancer.

Particularly, the present description relates to the use of such nucleic acids coupled with the compositions described herein as direct treatment of, for example, helicase overexpressing tumors or as radiosensitizing entities for palliative medicine. Moreover the composition and methods described herein can be used in conjunction with any other cancer treatment such as radiotherapy, surgery, hormonal treatment or conventional chemotherapy. The present description further provides compositions and methods for the enhancement of radiotherapy or used in combination with other treatment modalities.

The composition disclosed herein contains an RNAi inducing nucleic acid and a chitosan that has the following physicochemical properties: N:P ratio below 25, a chitosan with number average molecular weight (Mn) in the range of 5 kDa to 200 kDa and a degree of deacetylation in the range of 80% DDA to 95% DDA. The present description demonstrate the effectiveness of composition and methods to effectively transfect different cells line and induce gene silencing comparable to commercially available lipoplexes, where transfection efficiency reached 80% at the mRNA level and cell uptake 95% in some instance, without any apparent cytotoxicity.

RNA interference (RNAi) is a process by which double-stranded RNA directs sequence specific degradation of cellular transcripts such as messenger RNA (Sharp, 2001, Genes Dev, 15:485-490; Vance and Vaucheret, 2001, Science, 292:2277-2280). This phenomenon was initially discovered in *C. elegans* (Fire et al., 1998, Nature, 391:806-811). Naturally occurring RNAi is mediated by small double stranded fragments between 21-25 nucleotide and are termed small interfering RNA. These siRNA are generated by a dsRNA-specific endonuclease, called Dicer by a process cleaving long double stranded RNA (dsRNA) into a 21 base pair small interfering RNA (siRNA) consisting of a core region of 19 base pair duplex region flanked by two nucleotide 3' over hangs (Bernstein et al., 2001, Nature, 409:363-366). siRNA are then incorporated into the RNA-induced silencing complex (RISC), and direct RISC to recognize target mRNA with complementary sequences to the siRNA leading to the cleavage of the specific transcript.

Subsequently, RNAi was quickly recognized as having great potential in clinical applications since it was discovered that RNAi can be triggered in mammalian cells by introducing synthetic 21 nucleotide RNA duplexes (siRNA) (Elbashir et al., 2001, Nature, 411:494-498), thus bypassing the requirement of Dicer mediated processing of long dsRNA.

For example, by targeting and reducing the expression of ApoB, it is possible to prevent excess formation of VLDL, thus diminishing the accumulation of these atherogenic agents in the organism (Soutschek et al., 2004, Nature, 432:173-178). ApoB targeting at the mRNA level in non-human primate using sequence specific siRNAs demonstrated significant reductions in ApoB protein, serum cholesterol and low-density lipoprotein levels 24 h post-treatment (Zimmermann et al., 2006, Nature, 441:111-114). The therapeutic effect of such treatment using lipid based nanoparticles (SNALP-siRNA) lasted for 11 days at the highest siRNA dose, thus demonstrating an immediate, potent and lasting biological effect of siRNA treatment. Unfortunately, these lipid-based vectors produced a high level of liver toxicity as indicated by elevated serum levels of aspartate aminotransferase (AST) and alanine aminotransferase (ALT) suggested hepatocyte necrosis (Zimmermann et al., 2006, Nature, 441:111-114). Thus although these reports demonstrate the importance of ApoB as a target for atherosclerotic and CVD therapies, they also highlight the current inadequacies of siRNA delivery systems to attain a safe and efficacious reduction in systemic ApoB.

Direct delivery of RNAi in the form of synthetic small interfering RNA continues to be problematic, suffering from poor cellular targeting and uptake, a short half life due to intracellular and/or extracellular nuclease degradation (i.e. RNAse) as well as limited blood stability and toxicity (Stein, 1996, Trends Biotechnol, 14:147-149; Urban-Klein et al., 2004, Gene Therapy, 1-6; Katas and Alpar, 2006, J Control Release, 115:216-225). As a consequence, the translation of RNAi into a clinical therapeutic is still pending resolution of these issues. RNAi has been shown to operate in a wide variety of different cell types when introduced into cells by means such as transfection. However, transfection efficiency depends on the delivery vehicle carrying the small interfering RNA molecule. The delivery vehicle, referred to as the vector, should be able to condense, protect and carry siRNA into target cells. Once in the vicinity of the target, non-viral vectors should promote cellular uptake, avoid lysosomal sequestration and release their content in order to achieve the desired biological effect.

Chemical modification of synthetic siRNAs has provided resistance to nuclease degradation and improved blood stability. For example, selective addition of a phosphorothioate linkage or substitution with 2'-O-methyl on the C2 position of specific riboses increases nuclease resistance of siRNAs without compromising activity (Corey, 2007, J Clin Invest, 117:3615-3622; Whitehead et al., 2009, Nat Rev Drug Discov, 8:129-138; Judge et al., 2006, Mol Ther, 13:494-505). Nevertheless, some chemical modifications can increase cytotoxicity and off target effects and reduce mRNA hybridization (Weyermann et al., 2005, Eur J Pharm Biopharm, 59:431-438; Amarzguioui et al., 2003, Nucleic Acids Res, 31:589-595). Despite progress achieved through chemical modification to increase siRNA half life, transfection efficiency, cellular targeting and uptake remain as obstacles to effective delivery. Therefore, packaging systems which can both protect and transport chemically unmodified/modified siRNA to target cells are required. However, transfection efficiency depends on the delivery vehicle carrying the small interfering RNA molecule. The delivery vehicle, referred to as the vector, should be able to condense, protect and carry siRNA into target cells. Once in the vicinity of the target, non-viral vectors should promote cellular uptake, avoid lysosomal sequestration and release their content in order to achieve the desired biological effect. Such non-viral vectors are being tested in vitro and in vivo, demonstrating the potential translation of siRNA into a clinical reality. Nevertheless, major drawbacks are associated with such non-viral vectors. Low transfection efficiency, serum stability, aggregation and toxicity remain as major barriers to be addressed before commercialization of non-viral vectors as powerful and non-toxic tools for drug delivery in the clinic becomes a reality. The major classes of non viral vectors are discussed below:

Calcium Phosphate

The major drawback of this vector is limited efficiency and its inability to protect nucleic acids from nuclease degradation. Despite the improvement of its ability to protect nucleic acids, its transfection efficiency remains low thus preventing its effective use in vivo.

Cationic Lipids

Cationic lipids form complexes with nucleic acids via electrostatic interaction eventually forming multi lamellar lipid-nucleic acid complexes (lipoplexes). Liposome formulations usually include a cationic lipid and a neutral lipid such as DOPE (dioleoylphosphatidylethanolamine). The neutral lipid contributes to the stability of the liposomic formulation and facilitates membrane fusion as well as contributing to the lysozomal escape by destabilizing the endosome. Lipoplexes are one of the most efficient ways of delivering nucleic acids into cultured cells. Despite their transfection efficiency, lipoplexes are toxic as observed in cultured cells and confirmed by several in vivo findings. The toxicity is closely associated with the charge ratio of cationic lipids to nucleic acid in the complex as well as the administered dose. More biocompatible formulations are being tested and developed in order to reduce lipoplexes associated toxicity. Reduction of toxicity is mainly achieved via grafting with other polymers or reducing the total charge of the cationic polymer.

Cationic Polymers

Cationic polymers form nanoparticles of nanometric size through interactions between oppositely charged polycation and polyanion species (i.e. nucleic acids). These nanoparticles encapsulate nucleic acids, consequently preventing cargo degradation from nucleases (Romoren et al., 2003, Int J Pharm, 261:115-127). A large number of natural and synthetic cationic polymers have been used as vehicles for gene delivery or silencing. Many of these nanoparticles using cationic polymers have superior transfection efficiency and lower serum sensitivity compared to lipoplexes. Among naturally occurring polycation are proteins such as histones, cationized human serum albumin and chitosan, an aminopolysaccharide.

The group of synthetic polycations includes poly-L-Lysine (PLL), poly-L-Ornithine as well as polyamines such a polyethylenimine (PEI), polypropylenimine and polyamidoamine dendimers.

An advantage of polyplexes is that their formation does not require interaction of multiple polycations, contrary to the need of multiple lipid components of liposomes which make polyplex macroscopic properties easier to control. Another major advantage of polycation is their block structure therefore allowing direct chemical modification to attain higher efficiency or specific cell targeting. However, despite these advantages, many cationic polymers have been found toxic because of high surface charge density since high charge density nanoparticles appear to be more toxic. Furthermore, it has been reported that the charge density in the polymer plays a more important role in cytotoxicity than the total amount of charge. Toxicity may be molecular weight dependent as well, since the cytotoxicity of PEI increases linearly with molecular weight. Moreover, accumulation of non degradable polymer such as PEI in the lysosome, a phenomenon called lysosomal sequestration, may yet be an additional contributor to toxicity.

Chitosan is a natural polymer of glucosamine and N-acetyl-glucosamine monomers linked by $\beta$-1,4 glycosidic bonds derived from alkaline deacetylation of chitin. Chitosan molecular weight and degree of deacetylation dictate its biological and physicochemical properties. For example chitosan biodegradability is affected by the amount and distribution of acetyl groups. The absence of these groups or their random rather than block distribution results in very low rate of degradation.

Chitosan possesses a wide range of beneficial properties including biocompatibility, biodegradability, mucoadhesive properties, antimicrobial/antifungal activity and very low toxicity. Therefore, it has attracted attention of the pharmaceutical and biomedical field and became one of the most widely used non-viral vectors for nucleic acid packaging and condensation.

Several studies have addressed the effect of chitosan molecular weight and degree of deacetylation (DDA) on uptake of chitosan-plasmid DNA nanoparticle, nanoparticle trafficking and transfection efficiency on different cell lines. Huang et al. addressed this subject on A549 cells (2005, J Control Release, 106:391-406). However this study only used seven formulations (chitosan of 10,17,48,98 and 213 kDa at 88% DDA; 213 kDa at 61 and 46% DDA) to study the effect of average molecular weight (Mn) and DDA on transfection efficiency of pDNA without addressing the much smaller siRNA that is typically 21 bp versus thousands of base pairs in plasmids. They found that a decrease in Mn and DDA produces lower transfection efficiency for plasmids. However, the relationship between those two parameters is much more complex and demands a fine balance between chitosan Mn and DDA to achieve optimal stability. Their inability to draw a complex relationship is due to their limited number of formulations. Moreover, only one parameter at a time was varied preventing them to see a coupling effect between Mn and DDA in relation to the pH of the transfection media and to chitosan-to-DNA ratio (N:P). Another study addressing this complex relation for plasmid-chitosan polyplexes was performed by Lavertu et al. (2006, Biomaterials, 27:4815-4824). In their study, they varied the molecular weight, for several distinct DDA levels and also examined the chitosan-to-DNA ratio (N/P) and/or the pH of the transfection media. This study demonstrated that such optimization achieved high transfection efficiencies equivalent to broadly used commercial liposomes (Lipofectamine™ and Fugene™) in HEK293 cells.

The DNA binding capacity/affinity of chitosan increases when its degree of deacetylation increases to create a higher charge density along the chain to bind more tightly with pDNA to form nanoparticles (Ma et al., 2009, Biomacromolecules, 10:1490-1499). Thus chitosan with a very low DDA are unable to bind DNA efficiently and cannot form physically stable complexes to transfect cells (Koping-Hoggard et al., 2003, J Gene Med, 5:130-141). As mentioned hereinabove, DDA also exerts a dominant influence on biodegradability where high DDAs are difficult to degrade. In this light, a recent study by Koping-Hoggard et al. (2001, Gene Ther, 8:1108-1121) suggested that endosomal escape of the high Mn chitosan based complexes depends on enzymatic degradation of chitosan and would occur less readily with high DDA chitosans. The resulting degradation fragments are hypothesized to increase endosome osmolarity and lead to membrane rupture. Thus, for highly deacetylated chitosan (near 100% DDA), reduced degradability could result in reduced endosomal escape.

The influence of chitosan Mn on the ability to bind nucleic acids was evaluated in several studies. Binding affinity between oppositely charged macromolecules is strongly dependant on the valence of each molecule, with a low valence yielding only weak binding (Danielsen et al., 2004, Biomacromolecules, 5:928-936). The reduction in chitosan valence for lower molecular weight with shorter chains has been shown to reduce its affinity to DNA (Ma et al., 2009, Biomacromolecules, 10:1490-1499). Although a high level of complex stability is desirable extracellularly for protection against enzymatic attack, MacLaughlin et al. (1998, J Control Release, 56:259-272) suggested that a high Mn chitosan can form complexes that are overly stable to transfect cells since they cannot be disassembled once inside the cell. Furthermore, Lavertu et al. (2006, Biomaterials, 27:4815-4824) showed that Mn does not appear to be a dominant factor in cellular uptake but does appear to play a role in nucleic acid binding affinity and intracellular release. These interpretations and the need for a finely balanced intermediate stability of chitosan binding to nucleic acids were further supported by direct assessment of binding affinity by isothermal titration calorimetry (Ma et al., 2009, Biomacromolecules, 10:1490-1499) and by live intracellular imaging of polyplex trafficking and disassembly (Thibault et al., 2010, Mol Ther, 18:1787-1795).

The amine to phosphate ratio has been found to play an important role in DNA binding and nanoparticle formation. For example, increasing the N:P ratio enhances chitosan binding to DNA. For the same DDA, a lower Mn chitosan requires a higher N:P ratio to completely bind plasmid DNA. Similarly at equal Mn, a lower DDA requires a higher N:P ratio to completely bind DNA (Koping-Hoggard, 2003, J Gene Med, 5:130-141; Kiang et al., 2004, Biomaterials, 25:5293-5301). pH has been shown to play an important role in transfection efficiency. Lavertu et al. (2006, Biomaterials, 27:4815-4824) showed that complexes are more stable and an increase in transfection efficiency is achieved in slightly acidic medium. This can be explained by the fact that pH reduction increases chitosan protonation and consequently the positive charge on the polyplex (zeta potential) and the binding affinity of chitosan to DNA. The combined effect of the chitosan formulation parameters (DDA, Mn, N:P and pH) was studied for plasmid DNA delivery in vitro by Lavertu et al. (2006, Biomaterials, 27:4815-4824). They interestingly found that maximum transgene expression occurs for DDA: Mn values that run along a diagonal from high DDA/low Mn to low DDA/high Mn (Lavertu et al., 2006, Biomaterials, 27:4815-4824). Thus if one increases/decreases DDA, one must correspondingly decrease/increase Mn to maintain maximal transfection.

As mentioned above, pH plays an important role in transfection efficiency. Lavertu et al. (2006, Biomaterials, 27:4815-4824) showed that an increase in pH displaces the Mn for the most efficient formulation with plasmid DNA toward higher Mn because of the neutralisation of chitosan at higher pH resulting in reduced chitosan charge density. On the other hand, for a given DDA, a change in N:P ratio from 5:1 to 10:1 displaces the Mn for the most efficient formulation towards lower Mn, probably because of the stabilizing effect of increasing chitosan concentration. Thus, one can see the importance of these different formulation parameters on transfection efficiency and in the development of a more efficient and stable chitosan-DNA formulations.

The structural differences between pDNA and siRNA are believed to affect nanoparticle complexation/stability and the optimal parameters required for effective delivery. Chitosan has been used for siRNA delivery both in vitro and in vivo (de Fougerolles et al., 2007, Nat Rev Drug Discov, 6:443-453; Howard et al., 2006, Mol Ther, 14:476-484; Katas and Alpar, 2006, J Control Release, 115:216-225; Zimmermann et al., 2006, Nature, 441:111-114; and Liu et al., 2007, Biomaterials, 28:1280-1288). However, and despite attempts to identify optimal physico-chemical parameters for siRNA delivery, inconclusive results have been observed in the literature due to experimental discrepancies. For example, nanoparticle formation, stability and protection of the siRNA cargo was evaluated at pH 7.9; a pH that is unrepresentative of the physiological milieu. At this pH, chitosan is mainly deprotonated since its apparent pKa is close to 6.5, and thus unable to efficiently bind the siRNA cargo. Since complex formation was tested under these conditions, several groups have used high N:P ratios to compensate for the poor binding of chitosan to siRNA seen at pH higher than chitosan pKa. The use of these high pH values (i.e 7.9) represents an important design error and source of experimental discrepancy that led these investigators to use high N:P ratios to achieve nanoparticle complexation, stability and cargo protection. Unfortunately, the excess chitosan may competitively affect transfection efficiency, create multiple non-specific effects and increase toxicity leading to incorrect conclusions.

For example, it was reported that intermediate DDA (80%) and high Mn (64-170 kDa) were apparently more efficient than low molecular weight chitosan (10 kDa) in delivering siRNA (Katas et al., 2006, J Control Release, 115:216-225; and Liu et al., 2007, Biomaterials, 28:1280-1288). However, these high molecular weight chitosans were found to be toxic (Howard et al., 2006, Mol Ther, 14:476-484; and Richardson et al., 1999, Int J Pharm, 178:231-243). Additionally, all previous reports evaluating complex formation, other physico-chemical characteristics and transfection efficiency of chitosan/siRNA nanoparticles uniformly concluded that formulations were efficient only at very high N:P ratios (N:P>25) (Howard et al., 2006, Mol Ther, 14:476-484; Katas et al., 2006, J Control Release, 115:216-225; Liu et al., 2007, Biomaterials, 28:1280-1288). These reports did not recognize that a large portion of the excess chitosan is actually soluble and not a structural component of the nanoparticle (Ma et al., 2010, Biomacromolecules, 11:549-554). Such formulations with very high N:P ratios (N:P>25) display significant practical problems including limited dosing due to aggregation and non-specific toxic effects of large quantities of soluble chitosan.

The use here of appropriate pH conditions near chitosan pKa as well as near the physiological pH to assess nanoparticle physicochemical characteristics revealed that such high N:P were not required to form efficient nanoparticle delivery vehicles, as demonstrated in the present disclosure (FIG. 3).

Chitosan was used to deliver pharmacologically active compounds through different administrational routes including intranasal, oral, intraperitoneal, and intramuscular routes. Chitosan/Insulin was administered through intranasal routes in rat and sheep. These formulation involved the use of a water soluble chitosan of molecular weight of 10 kDa or greater, with no specification on degree of deacetylation (Ilium, 1996, Danbiosyst UK Limited, United States, vol. 5554388; 1998, Danbiosyst UK Limited, United States, vol. 5744166).

Chitosan has also been used as adjuvant for the immunization of mice through an intranasal route with soluble formulations (US patent application publication no. 2003/0039665). These formulations involved chitosan glutamate with a Mn ranging between 10-500 kDa with a degree of deacetylation between 50-90%.

Chitosan has also been used to deliver nucleic acids varying from plasmid DNA to siRNA in vitro and in vivo as well. More than 40 examples of in vivo studies using siRNA with various delivery vehicles have been reported (de Fougerolles et al., 2007, Nat Rev Drug Discov, 6:443-453) to treat ocular (Nakamura et al., 2004, Mol Vis, 10:703-711) and pulmonary targets (Howard et al., 2006, Mol Ther, 14:476-484), or directed towards the nervous system (Kumar et al., 2006, Plos Medicine, 3:505-514), liver (Soutschek et al., 2004, Nature, 432:173-178), tumors (Grzelinski et al., 2006, Hum Gen Ther, 17:751-766) and other organs by local or systemic delivery. In one example, chitosan/siRNA nanoparticles mediated TNF-α knockdown in peritoneal macrophages for anti-inflammatory treatment in an arthritis murine model (Howard et al., 2006, Mol Ther, 14:476-484).

Several studies have examined the ability of chitosan to deliver siRNA in vitro and in vivo. Katas et al. (2006, J Control Release, 115:216-225), used two different forms of chitosan salts (CS-HCl and CS-Glutamate) with a DDA of 84% to study the influence of chitosan parameters on transfection efficiency. Four different high molecular weight chitosans were used (470 kDa, 270 kDa, 160 kDa and 110 kDa) and they found that increasing chitosan concentration from 25 µg/ml (1.25:1) to 300 µg/ml (15:1) increased nanoparticle size from approximately 150 nm to 450 nm (Katas et al., 2006, J Control Release, 115:216-225).

Moreover, it was shown in their study that chitosan-glutamate yielded smaller nanoparticles than chitosan-HCl. Katas et al. (2006, J Control Release, 115:216-225) found—under their experimental conditions—that complete binding of siRNA to chitosan occurred only at an N:P ratio of 100:1 and above, conditions of extreme excess of chitosan where most likely >95% of the chitosan is soluble and not complexed to siRNA (Ma et al., 2010, Biomacromolecules, 11:549-554). This large quantity of excess moderate DDA (84%) chitosan is expected to cause sustained inflammation in vivo and to increase adverse immunological responses (Jean et al., 2009, Gene Ther, 16:1097-1110). In their study, chitosan glutamate with a molecular weight of 470 kDa showed the highest gene silencing effect at 24 h post-transfection in vitro compared to its lower molecular weight or chitosan hydrochloride (Katas et al., 2006, J Control Release, 115:216-225). Ionic gelation of chitosan glutamate with an average molecular mass of 470 kDa showed a higher silencing efficiency (82% mRNA knockdown) than chitosan—siRNA nanoparticles formed by simple complexation (51% mRNA knockdown) (Katas et al., 2006, J Control Release, 115:216-225).

Another group led by Howard et al. (2006, Mol Ther, 14:476-484), delivered chitosan—siRNA nanoparticles in a transgenic EGFP mouse model via the intranasal route of administration. For their study, they used chitosan at 84% DDA and 114 kDa at four different N:P ratios (N:P 6, 33, 71 and 285). Higher N:P ratios resulted in smaller nanoparticles (N:P 6=223.6 nm vs N:P 33=181.6 nm) at low chitosan concentration of 250 µg/ml (Howard et al., 2006, Mol Ther, 14:476-484). The same pattern was observed at higher chitosan concentration (1 mg/ml) where chitosan nanoparticles with a DDA of 84%, Mn of 114 and an N:P ratio of 33 had an average diameter of 328 nm compared to 139 nm for the formulation 84-114-285 (Howard et al., 2006, Mol Ther, 14:476-484).

Their preliminary in vitro study showed that nanoparticle size depends on the N:P ratio and increases in the size at lower N:P ratios, suggesting high N:P ratios to be required. This finding is in contradiction to the findings presented herein, where it is demonstrated below the critical role of pH when evaluating chitosan-siRNA complexation and stability. Based on their findings, cell uptake and silencing efficiency were measured at the high N:P ratios of 36 and 57 respectively in NIH 3T3 and H1299 cell lines. Chitosan formulations at the high N:P ratio of 36 was used to study the silencing efficiency of EGFP stable cell lines. Silencing efficiency was 77.9% and 86.9% in H1299 and primary peritoneal mouse macrophage, respectively. The in vivo silencing efficiency of the chitosan formulation 84-114 at N:P 36 achieved 43% silencing efficiency in EGFP transgenic mouse model following a 30 µg siRNA injection/day for five days compared to untreated controls (Howard et al., 2006, Mol Ther, 14:476-484).

In another in vivo study by Howard et al. (2009, Mol Ther, 17:162-168), a 27 base-pair siRNA targeting TNF-α mRNA was complexed to chitosan 84-114 at the N:P ratio of 63 and injected in a collagen induced arthritis (CIA) mouse model. Their formulation achieved 43% silencing as measured by TNF-α plasma levels.

Ji et al. (2009, Nanotechnology, 20:405103) suggested that 190 kDa and 310 kDa chitosans at DDA ranging from 75% to 85% are suitable delivery vehicles for siRNA. Similarly to the above studies, Ji et al. used chitosan formulations at a high N:P ratio of 50 for knockdown experiments of the FHL2 oncogene in Lovo cells. Their formulations achieved 69% of mRNA knockdown.

In an attempt to identify optimal parameters for chitosan delivery of siRNA, Liu et al. (2007, Biomaterials, 28:1280-1288), tested a range of chitosan with different DDA, Mn and N:P ratios and stated that N:P ratio>25 are needed for efficient silencing. They also found that low molecular weight chitosan-siRNA (10 kDa) formulations prepared at N:P 50 showed no knockdown of endogenous EGFP in H1299 human lung carcinoma cells, whereas chitosan formulations prepared with higher Mn (64.8-170 kDa) at DDA of 80% showed greater gene silencing ranging between 45% and 65%. The highest gene silencing efficiency (80%) was achieved using chitosan/siRNA nanoparticles at the extreme N:P 150 with Mn of 114 and 170 kDa respectively and DDA of 84% that correlated with their assessments of stable formation of nanoparticles with a diameter of approximately 200 nm. Additionally, Liu et al. (2007, Biomaterials, 28:1280-1288) found that a 95% DDA and 9 kDa chitosan complexed to anti-EGFP siRNA at N:P ratio of 50 had an undesirable large size of 3500 nm as measured by dynamic light scattering (DLS). Furthermore, they stated that this specific formulation did not form complexes with siRNA at N:P ratio as high as 50 according to their gel retardation assays for stability testing conducted at the basic pH of 7.9 that was shown here to produce artifactual particle disassembly. In addition, this specific formulation showed no EGFP knockdown when compared to the negative untreated control.

The above results found by others are in contrast to the novel findings presented herein where it is demonstrated that chitosan-siRNA nanoparticles can be formed at moderate to low N:P ratios (below 25 and preferably 5) using chitosan with a range of molecular weights (5 to 200 kDa) at DDAs between of 80% and 95% and these nanoparticles achieve high levels of gene silencing, good stability and small size ranges compared to previously reported systems.

Chitosan coated poly(isohexyl cynoacrylate) (PIHCA) nanoparticles have also been used to deliver intravenously anti-RhoA siRNAs entities in a xenografted aggressive breast cancer model (Pille et al., 2006, Hum Gen Ther, 17:1019-1026). Administration of chitosan-coated-PI HCA-anti-R hoA siRNA nanoparticles significantly reduced cancer aggressivity in vivo by knockdown of over-expressed RhoA in the cancer cells. Zhang et al. studied Nanogene 042, a chitosan derived formulation, for de novo expression of siRNA targeting the NS1 protein in lung tissues for the prevention and treatment of Respiratory Syncitial Virus (RSV) infections in a Balb/c model (Zhang et al., 2005, Nat Med, 11:56-62). Zhang et al. used shRNA based plasmids and observed an efficient silencing of the NS1 gene and an attenuation of RSV infection coupled with a lowered viral titer load in vivo. Nanogene 042 showed higher transfection efficiency and induced less inflammation compared to classical high MW chitosan (Zhang et al., 2005, Nat Med, 11:56-62). However, the molecular weight of Nanogene 042 is not disclosed in the stated reference.

For the purpose of the present description, the C57BL/6 (C57BL/6NCrI) mouse model is used for enabling different embodiments. The C57BL/6 mouse model was developed by Charles River and Research Diets. The C57BL/6 mouse model can become obese when fed a fat rich diet (D12492) with an apparent weight gain two weeks following with a fat rich diet compared to lean control. The C57BL/6 mouse model is used in multipurpose studies and hyperlipidemia research to study the level of LDL cholesterol in circulation during a high-fat diet (Soutschek et al., 2004, Nature, 432:173-178; Crooke et al., 2005, J Lipid Res, 46:872-884; Bose et al., 2008, J Nutr, 138:1677-1683). The fat rich diet (D12492) is equivalent to six times more fat than the control diet D12450B which contains only 10 kcal % fat. In addition, the fat rich diet D12492 contains 300.8 (mg)/kg of cholesterol compared to 18 (mg)/kg for the control diet D12450B. Thereby, the feeding with such a high fat chow creates instability in the accumulation of LDL in arteries versus its elimination in the liver, driving the development of atherosclerosis in the C57BL/6 mouse model.

It has been found as described herein below that the compositions described herein are effective gene transfer vectors when combined with siRNA achieving in vitro transfection efficiencies similar to the commercial liposome DharmaFECT™. Moreover, the compositions not only achieved comparable efficiency in delivering siRNA into cells and similar silencing as DharmaFECT™, but with lower toxicity.

Figure 7A:
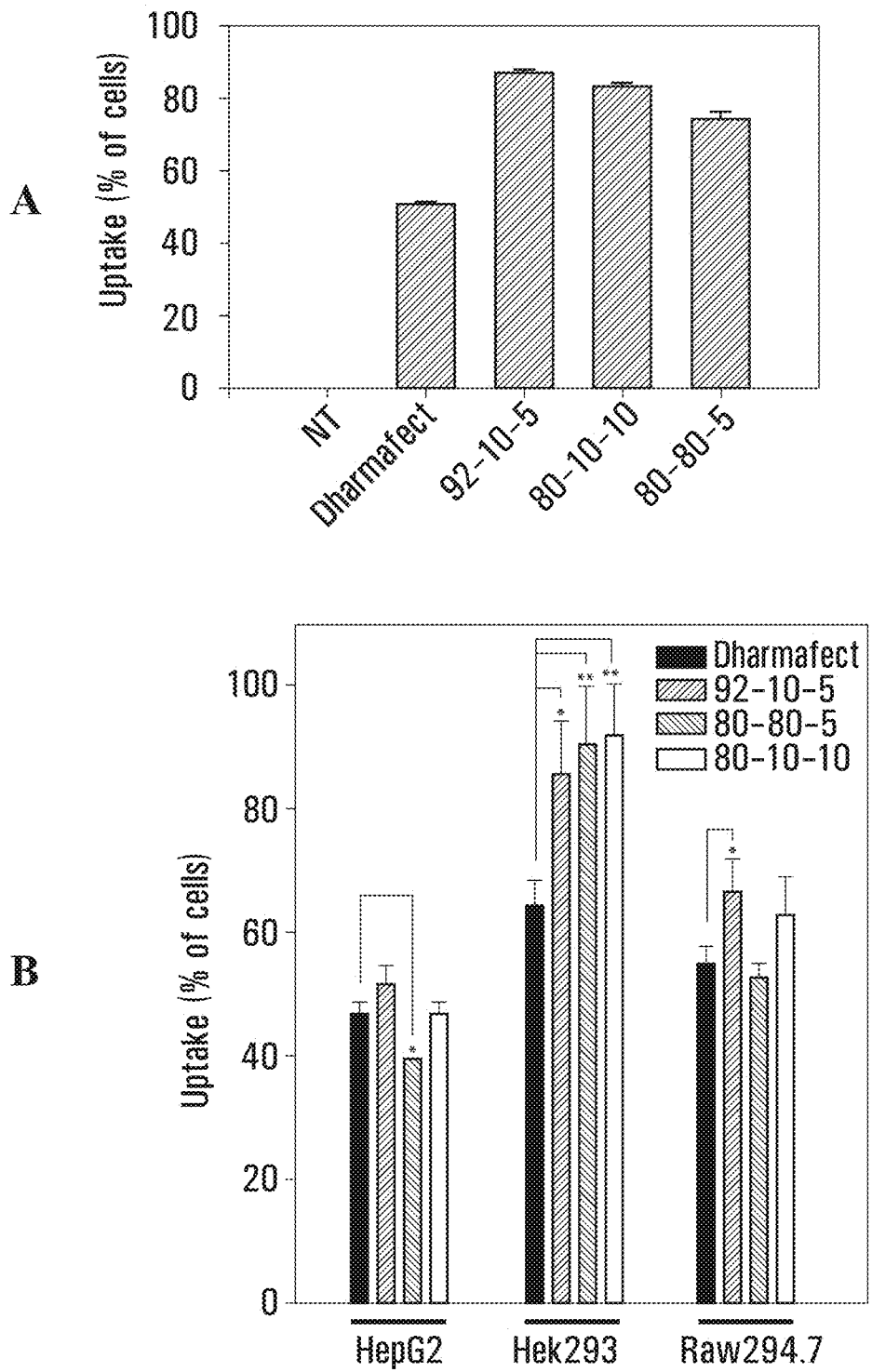
FIG. 7A illustrates histogram representations of the cellular uptake of dsODN/nanoparticles 24 hours post-transfection in several cell lines: (A) Chitosan (92-10-5, 80-80-5 or 80-10-10)/5'-6FAM labeled dsODN DPP-IV uptake in HepG2 cell lines; and (B) Chitosan (92-10-5, 80-80-5 or 80-10-10)/5'-6FAM labeled dsODN-ApoB uptake in HepG2, HEK293 and RAW264.7 cells, DharmaFECT® #1 and 4 were used as positive uptake control.
Figure 7B:
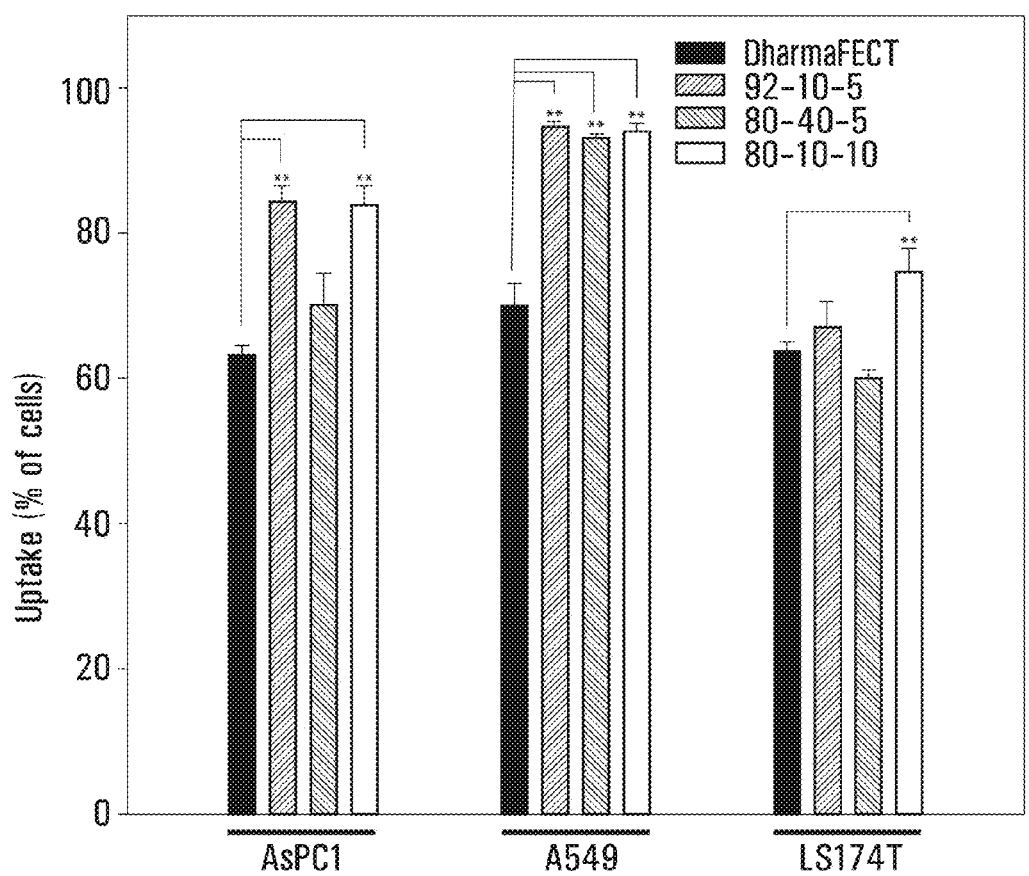
FIG. 7B illustrates a histogram showing the cellular uptake of dsODN/nanoparticles 24 hours post-transfection in several cell lines, chitosan (92-10-5, 80-40-5 or 80-10-10)/5'-6FAM labeled dsODN RecQL1 uptake in AsPC1, LS174T and A549 cell lines, DharmaFECT™ #1 was used as positive uptake control.
Figure 8:
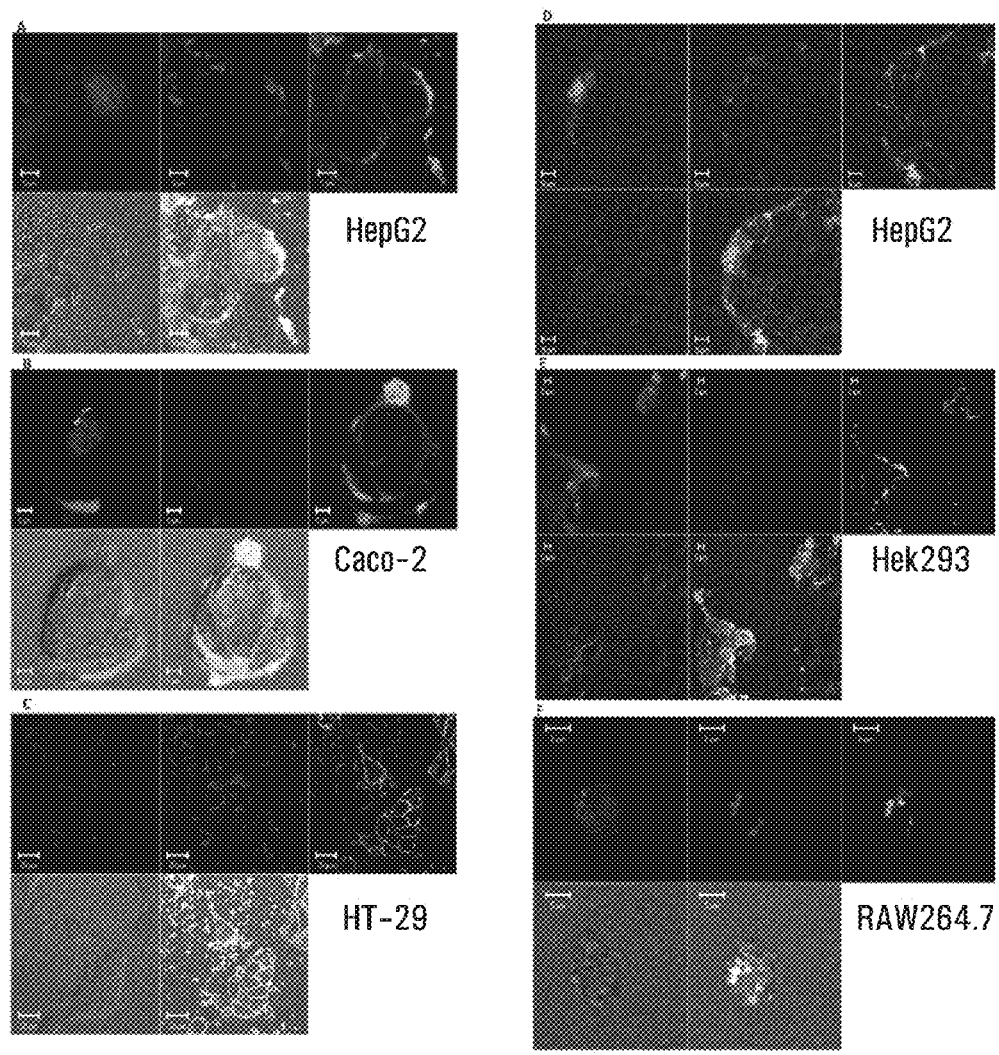
FIG. 8 illustrates confocal imaging of chitosan/siRNA nanoparticle uptake 24 hours post-transfection in (A) HepG2, (B) Caco-2 and (C) HT-29 cell lines transfected with chitosan/dsODN-DPP-IV nanoparticles, (D) HepG2, (E) HEK293 and (F) RAW264.7 cell lines transfected with chitosan/dsODN-ApoB nanoparticles. Chitosan 92-10 (DDA, Mn) was labeled with rhodamine (red) and dsODN were 5' labeled with 6FAM (green). Chitosan 92-10 was complexed to siRNA at an N:P ratio of 5. Cell membranes were stained prior to imaging with CellMask™ (blue), a membrane anchoring amphipatic dye, to differentiate between internalized and membrane bound nanoparticles. Images shown represent each separate channel with dsODN in green, chitosan in red, membrane in blue, transmission DIC in grey and the merged images shown on the bottom left quadrant.

Uptake efficiency using chitosan/dsODN nanoparticles achieved levels comparable to or higher than the commercially used lipoplex (DharmaFECT™) with similar relative variation between cells type (FIGS. 7A and 7B). Furthermore, these results are in accordance with confocal microscopy data (FIG. 8), described below, where images show a cellular distribution of chitosan and dsODN for all cell lines indicating a qualitative correlation to the FACS quantitative data. It is demonstrated herein the capability of the formulations described to transfect and efficiently deliver different siRNA into multiple cell lines (see for example FIGS. 7A and 8).

Results disclosed herein clearly reveal the effectiveness of the described chitosan-based formulations to efficiently deliver siRNA and knock down specific genes at N:P ratios far below those used previously in the art. In general, all of the low N:P ratio chitosan formulations used herein reached high level of gene silencing.

Figure 1B:
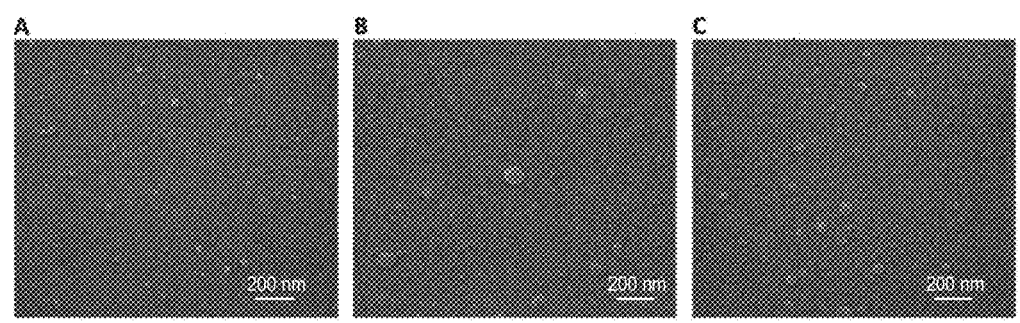
FIG. 1B illustrates environmental scanning electron micrograph (ESEM) images of spherical chitosan/dsODN nanoparticles and population size distribution: (A) 92-10-5 chitosan/dsODN-RecQL1 nanoparticles, (B) 80-40-5 chitosan/dsODN-RecQL1 nanoparticles, and (C) 80-10-10 chitosan/dsODN-RecQL1 nanoparticles.
Figure 2A:
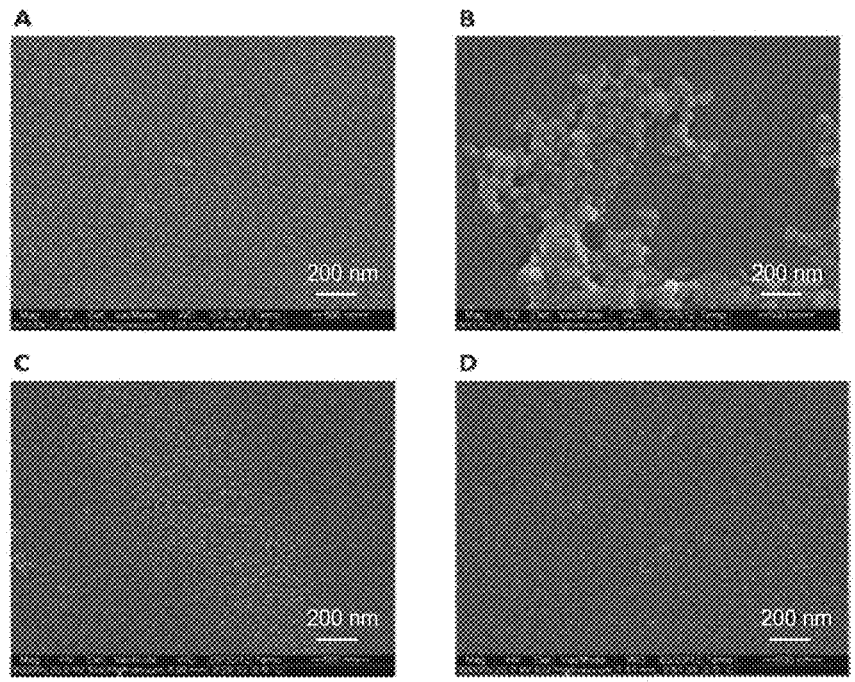
FIG. 2A illustrates environmental scanning electron microscopy (ESEM) images of spherical chitosan/siRNA nanoparticles and population size distribution of (A) 80-10-5 chitosan/siRNA-ApoB nanoparticles, (B) 80-40-5 chitosan/siRNA-ApoB nanoparticles, (C) 92-10-5 chitosan/siRNA-ApoB nanoparticles and (D) 92-40-5 chitosan/siRNA-ApoB nanoparticles.
Figure 2B:
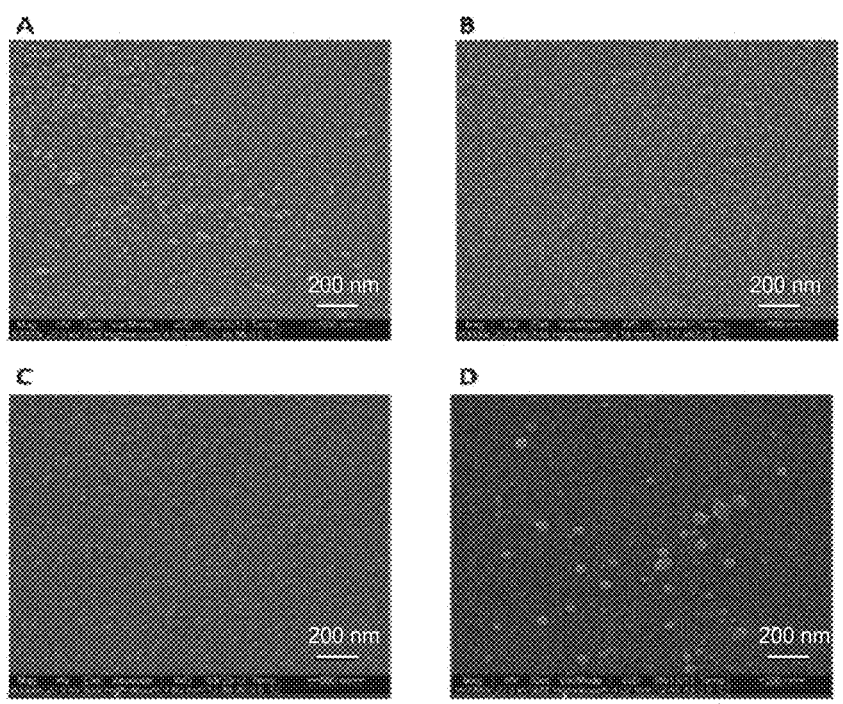
FIG. 2B illustrates environmental scanning electron micrograph (ESEM) images of spherical chitosan/siRNA nanoparticles and population size distribution: (A) 80-10-5 chitosan/siRNA-MDR1 nanoparticles, (B) 80-200-5 chitosan/siRNA-MDR1 nanoparticles, (C) 92-10-5 chitosan/siRNA-MDR1 nanoparticles and (D) 92-150-5 chitosan/siRNA-MDR1 nanoparticles.

The results show nanoparticles of spherical shape (FIGS. 1 and 2) with mean diameters ranging between 45-156 nm (Table 2) depending on the chitosan formulation (80-10-5, 80-40-5, 92-10-5, 92-40-5, 80-10-10, 80-80-5, 92-150-5 and 80-200-5) used and the extent of chemical modification of the siRNA. No statistical differences in nanoparticle size were observed between dsODN and un-modified siRNA-ApoB (Seq1, SEQ ID NO:5) and moderately modified siRNA-ApoB complexed to chitosan (Seq2, SEQ ID NO:6 and SEQ ID NO:7). Whereas, fully modified siRNA sequence yielded larger nanoparticles when complexed to the different chitosans.

Results obtained with specific formulations described herein are consistent with dynamic light scattering results obtained (Table 2), thereby indicating the robustness of the composition and method described herein. Furthermore, the nanoparticles formed yield reproducible sizes below 200 nm allowing for avoidance of renal clearance thus improving in vivo transfection efficiency and increasing circulating nanoparticles half-life.

Chitosan/siRNA stability was evaluated using the Ribogreen Assay™, a fluorescence based assay, to quantitate the released siRNA following complex destabilization. The results show that chitosan/siRNA nanoparticle with an N:P ratio of 5 and 10 were stable for up to 20 hours at pH 6.5. Chitosan 80-10-5 showed the least stability when compared to other formulations. Increasing the N:P ratio for chitosan 80-10 resulted in an improvement of nanoparticle stability. Except for chitosan 80-10, increasing the N:P ratio above five did not result in an increase of nanoparticle stability (see for example FIG. 4A).

It is demonstrated that the formulations described herein can achieve levels of gene silencing comparable to the commercial liposome DharmaFECT™ without any apparent cytotoxicity. The results disclosed herein clearly reveal the effectiveness of the described chitosan-based formulations to efficiently deliver siRNA and knock down specific genes at N:P ratios (N:P=5) far below those used previously by others (N:P>20) (see for example FIGS. 11A and 11B). In general, all of our low N:P ratio chitosan formulations reached high levels of gene silencing supporting the FACS data (see for example FIGS. 7A and 7B). A tendency for the low molecular weight (10 kDa) and high DDA (92%) chitosan to be most efficient (FIGS. 11 and 12) and smaller (FIG. 4B) was found suggesting a particularly optimal formulation at NP ratio 5.

Figure 13:
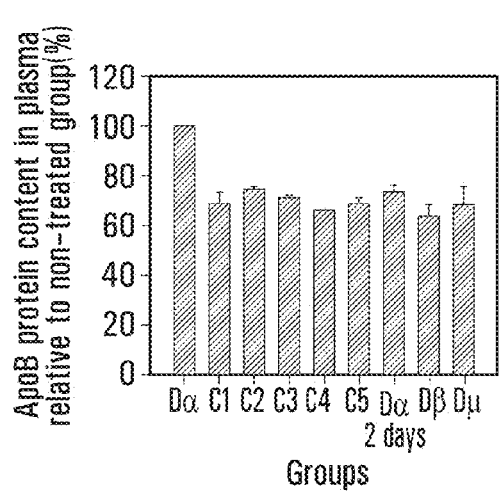
FIG. 13 illustrates a histogram showing effects of chitosan/siRNA administration on ApoB plasma levels. Protein levels were measured by ELISA, for each treatment group. Columns and error bars represent the mean protein level relative to the untreated atherosclerotic group, Dα. The group Dμ is the normal negative control group fed a normal low fat diet.
Figure 14:
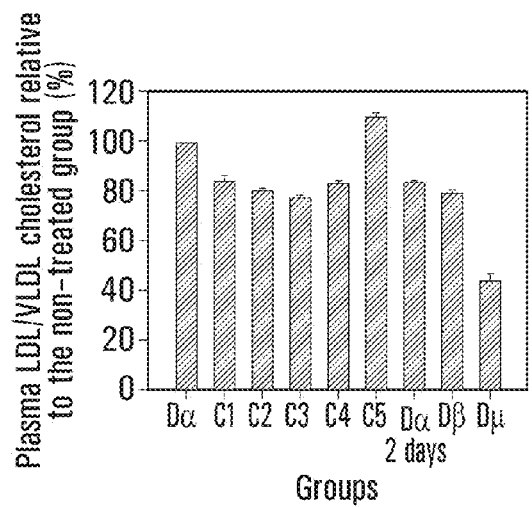
FIG. 14 illustrates a histogram showing the therapeutic lowering of LDL/VLDL cholesterol after chitosan/siRNA administration. LDL/VLDL cholesterol levels were measured by a quantitative colorimetric ELISA kit on samples taken the day of euthanasia. Columns and error bars represent the mean cholesterol levels relative to the untreated atherosclerotic group, Dα. The group Dμ is the normal negative control group fed with a normal low fat diet.

It has also described that the composition described herein for the treatment of atherosclerosis reduced in vivo ApoB plasma levels by approximately 30% compared to the positive untreated control (called Dα below) (FIG. 13). It is also demonstrated that such a reduction resulted in ApoB serum levels similar to those of the non-atherosclerotic animal group negative control, and is thus in the therapeutic range. It is also demonstrated in the present description that the composition described herein for the treatment of atherosclerosis produced a 20% reduction in LDL-cholesterol without any apparent toxicity (FIG. 14). It is also demonstrated that chitosan based therapeutic nanocomplexes containing siRNA (TNCs) did not result in any liver toxicity as demonstrated by normal ALT/AST levels in serum.

Figure 15:
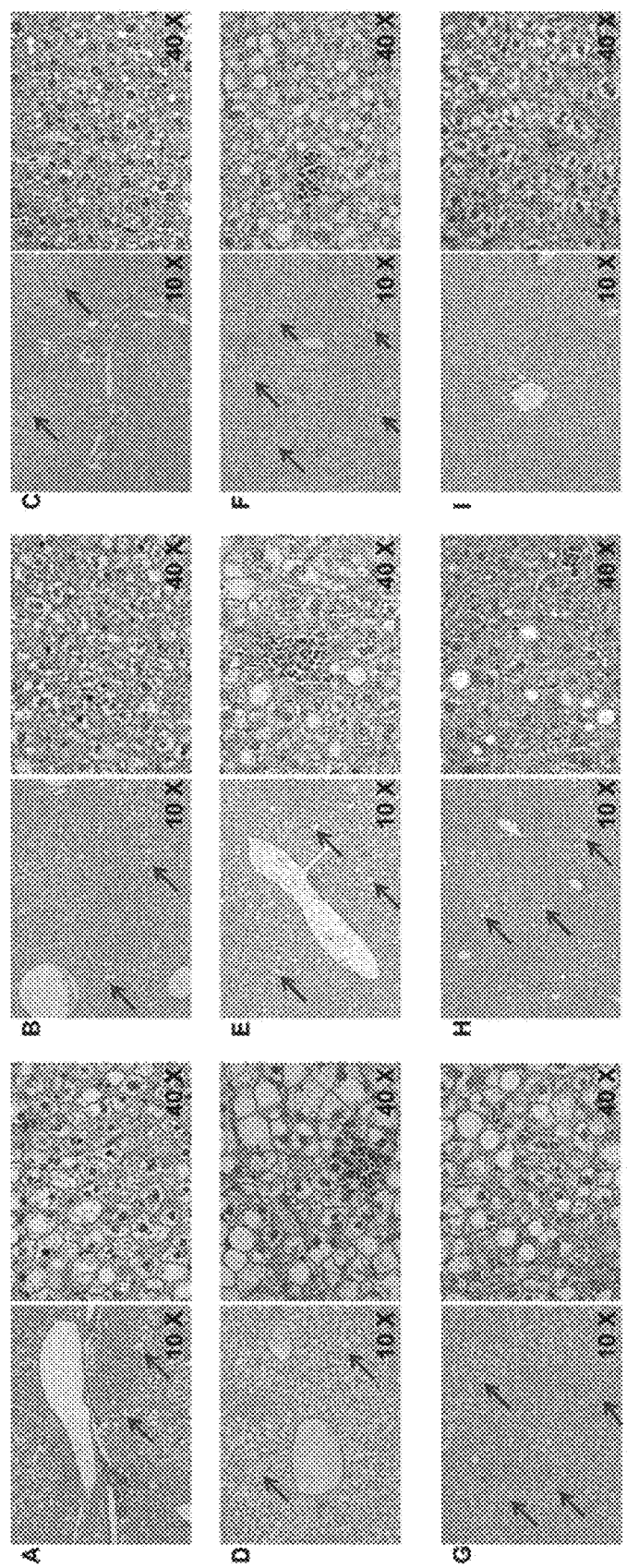
FIG. 15 illustrates the reduction of liver cholesterol droplets in Therapeutic NanoComplex (TNC) treated animal livers. Hematoxylin-eosin stained paraffin fixed liver sections of (A) C1-1, (B) C2-1, (C) C3-1, (D) C4-1, (E) C5-1, (F) Dα-2 day, (G) Dα-3, (H) Dβ-1 and (I) Dμ-1 mice demonstrating the effects of chitosan/siRNA administration in cholesterol accumulation in the liver. Arrows (→) indicate cholesterol droplet accumulation. The Dα group is the positive untreated atherosclerotic control while Dμ is the normal negative control fed with a low fat diet.
Figure 16:
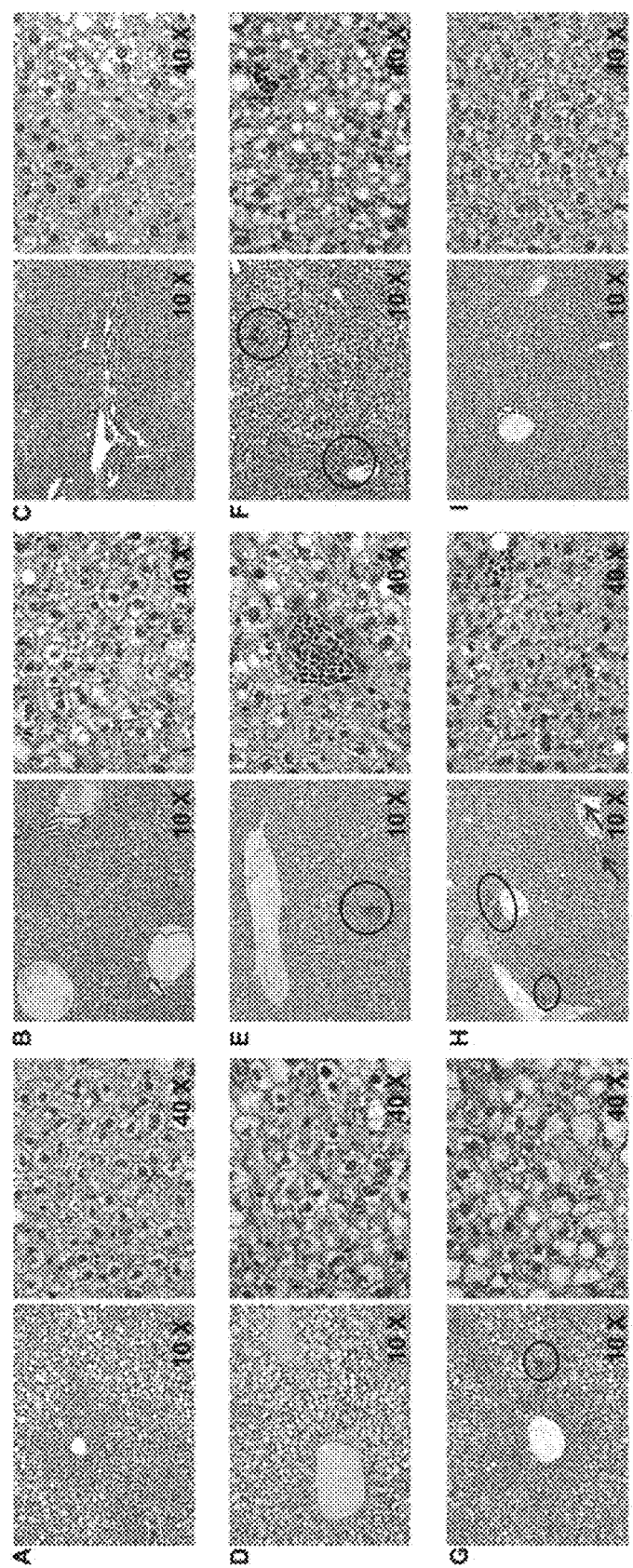
FIG. 16 illustrates resorption of inflammation in TNC treated animal liver. Safranin-O/fast-green/iron-hematoxylin stained paraffin fixed liver section of (A) C1-1, (B) C2-1, (C) C3-1, (D) C4-1, (E) C5-1, (F) Dα-2 day, (G) Dα-3, (H) Dβ-1 and (I) Dμ-1 mice demonstrating the resorption of the inflammatory reaction related to the chitosan/siRNA administration or atherosclerosis development. Circles (○) and arrows (→) indicate lymphoid infiltration.

It is further demonstrated that TNC treatment had a therapeutic effect on cholesterol accumulation in the liver three weeks post injection, where cholesterol accumulation in TNC treated animal liver was significantly reduced (FIG. 15). Similarly, chitosan based TNCs induced transient immune cell infiltration into the liver which resorbed rapidly without toxicity as demonstrated in another embodiment herein (FIG. 16). The lack of liver toxicity and the rapid resorption of immune cell infiltration indicated the possibility of increasing the injected dose to achieve yet higher ApoB and LDL-C plasma reduction.

Furthermore, it is described that naked siRNA without chitosan targeting ApoB induced an intense inflammatory response thus limiting their dosing and potential for therapeutic use in an uncomplexed form. The lack of toxicity/inflammation in TNCs treated animal at a tested dose of 1 mg/kg anti-ApoB siRNA coupled with their ability to reduce ApoB plasma levels by 35% indicates their importance and potential use in a dose response study to determine the maximal tolerated dose (MTD) and achieve higher ApoB plasma reduction.

It is demonstrated that TNC-treated animals had reduced ApoB plasma levels for at least 8 weeks following the third and last injection. Reductions in ApoB plasma levels for low N:P chitosan-based TNCs were maintained for more than seven weeks after the last injection in the C1 animal group (FIGS. 13 and 16) without any apparent inflammation or liver toxicity. These results indicate a particularly promising longevity of TNC treatment and effective controlled release properties.

It is thus disclosed herein that low N:P chitosan ApoB siRNA TNCs described herein, achieved a ~35% reduction of ApoB plasma levels and a ~20% reduction in LDL/VLDL cholesterol reduction at a 1 mg/kg injected dose (FIGS. 13 and 14). These results suggest an effective therapeutic result has been obtained since previously claimed successful results published using liposomal delivery systems for ApoBsiRNA required higher doses to achieve similar or higher ApoB/LDL-VLDL cholesterol reduction and these doses were associated with liver toxicity and increased ALT and AST levels (Zimmermann et al., 2006, Nature, 111-114; Soutschek et al., 2004, Nature 432:173-178). For example, the use of 5 mg kg$^{-1}$ of siRNA coupled with a lipid formulation (SNALP) achieved a 73% reduction in ApoB plasma levels (Zimmermann et al., 2006, Nature, 111-114); this fivefold higher injected concentration achieved 2.5 fold higher ApoB plasma reduction compared to the results of the present invention. Furthermore, the use of siRNA targeting ApoB in Ldlr −/+, Cetp −/− mice model using a second generation lipid LNP-OCD (LNP201) developed by Merck Inc. showed an approximately 70% reduction in LDL at 3 mg kg$^{-1}$ (Tadin-Strapps et al., 2011, J lipid Res, 52:1084-1097). Additionally, 50 mg kg$^{-1}$ of naked cholesterol modified siRNA were required to achieve 68% and 31% reduction in ApoB plasma level depending on the siRNA sequence used (Soutschek et al., 2004, Nature, 173-178). Additionally these studies were performed in normal C57BL/6 mice fed with regular chow (lean control) on the contrary to enclosed study where C57BL/6 mice groups were fed high fat diet to simulate atherosclerosis until the completion of the study.

Furthermore, intraperitoneal administration of anti-ApoB antisense oligonucleotiode (AOS) ISIS-147764, currently in phase III clinical trial, required at least 25 mg kg$^{-1}$ administered twice weekly to C57BL/6 feed with high fat in order to achieve a 55% in ApoB plasma reduction level after six to eight week of treatment. Additionally, Crooke et al. reported a plasma cholesterol return to normal following 50 mg kg$^{-1}$ administration twice per week for six to eight weeks (Crooke et al., 2005, J Lipid Res, 46:872-884). The effect of ISIS-147764 on cholesterol plasma reduction was observed on the fourth week of treatment (50 mg kg$^{-1}$ twice/week).

The compositions and methods described herein demonstrate clearly the efficiency of ApoB reduction using relatively low doses (1 mg kg$^{-1}$) when compared to prior art. Additionally, it becomes clear in the present description that increasing dose using the present disclosure and disclosed TNCs will lead to an enhanced ApoB and LDL/VLDL-C plasma reduction since ApoB reduction has been always shown to be dose-dependent (Zimmermann et al., 2006, Nature, 441:111-114; Soutschek et al., 2004, Nature, 432: 173-178; Crooke et al., 2005, J Lipid Res, 46:872-884; and Crooke, 2005, Expert Opin Biol Ther, 5:907-917).

The present description provides methods for treatment of diabetes mellitus and related conditions and symptoms. Such diabetes mellitus and related conditions include insulin-dependent diabetes mellitus (type I diabetes), noninsulin-dependent diabetes mellitus (type II diabetes), insulin resistance, hyperinsulinemia, and diabetes-induced hypertension. Other diabetes-related conditions include obesity and damage to blood vessels, eyes, kidneys, nerves, autonomic nervous system, skin, connective tissue, and immune system. The composition described herein can be used either alone or in combination with insulin and/or hypoglycemic compounds.

The present description provides methods for treatment of cancer. Such cancer include breast cancer, glioma, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, Hodgkin's disease, non-Hodgkin's lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma, testicular cancer, oral cancer, pharyngeal cancer, pediatric neoplasms, leukemia, neuroblastoma, retinoblastoma, glioma, rhabdomyoblastoma and sarcoma.

One approach to circumvent MDR is the use of P-gp modulators or reversal agents compounds that inhibit the transport activity of P-gp. However, their pharmacokinetic interaction with chemotherapeutics and toxicities limit their usage in clinics. Alternatively, the expression of P-gp can be inhibited by RNA interference (RNAi). Unlike chemical regulators, this technology may provide a more specific approach to downregulation of P-gp and resistance reversal.

Various studies using siRNA or shRNA have demonstrated the potential use of RNAi to overcome multidrug resistance phenotype. The first studies showing the proof of principle of RNAi mediated reversal of resistance by p-gp inhibition were published in 2003 (Nieth et al., 2003, FEBS letters 545(2-3):144-150) and (Wu et al., 2003, Cancer research 63(7):1515. Both studies used a transient approach with siRNA to modulate multidrug resistant phenotype in different cell models. Using 200 nM of siRNA, Hao et al. were able to suppress p-gp levels by 65% in MCF-7/ADR and A2780 Dx5, to highly resistant MDR cell lines. Furthermore, they showed that MDR1 targeted siRNA reversed resistance to p-gp transportable drugs (Doxorubicin) but did not affect the sensitivity to hydroxyurea a non P-gp substrate. These data suggest that silencing of P-gp expression mediated by siRNA is specific. However, the most pronounced transient MDR reversal of nearly 90% was achieved in the pancreatic carcinoma derived cell line (EPP85-181RDB) and gastric carcinoma cell (EPG 85-257RDB) despite the use of smaller concentration of siRNA (100 nM) (Nieth et al., 2003, FEBS letters 545(2-3):144-150. Recently, Dönmez et al. (2011, Biomedicine and Pharmacotherapy 65(2):85-89) revealed 89% in gene silencing activity of MDR1 in doxorubicin-resistant MCF-7 cell although the concentration was lower as 20 nM. These data indicate that the efficacy of RNAi may be siRNA sequence-dependent as well as cell line-dependent.

In addition to siRNA, stable antiMDR1/P-gp shRNA expression vectors were used to modulate the MDR phenotype. In one study, shRNA expression had similar efficiency compared to siRNA to down regulate MDR1/P-gp in the paclitaxel-resistant SKOV-3TR and OVCAR8TR ovarian cancer cell lines (Duan et al., 2004, Molecular cancer therapeutics 3(7):833). Furthermore, Stege et al. (2004, Cancer gene therapy 11(11):699-706) reported a complete reversal of P-gp expression by introducing a shRNA-expressing vector (psiRNA/MDR-A) into an extremely high drug-resistant human gastric carcinoma cell line EPG85-257RDB. Similarly, Yaglie et al. (2004, Gene therapy 11(14):1170-1174) observed a complete reversal of doxorubicin resistance in K562 leukaemic cells by introducing the shRNA-expressing vector pSUPER. Using the same approach, Shi et al. (2006, Cancer biology & therapy 5(1): 39-47) showed also a stable downregulation of MDR1/P-gp gene expression and function induced by endogenous expression of shRNA which expressed a novel containing MDR1-siRNA expression cassette and EGFP expression gene in human epidermoid carcinoma cell lines (KBv200).

In all of the above mentioned studies, Lipofectamine 2000 (Li et al., 2006, European journal of pharmacology, 536(1): 93-97) and (Dönmez, Y. and U. Gündüz, 2011, Biomedicine & Pharmacotherapy 65(2):85-89) and oligofectamine (Nieth et al., 2003, FEBS letters 545(2-3):144-150; Wu et al., 2003, Cancer research 63(7):1515; Stierle et al., 2005, Biochemical pharmacology 70(10):1424-1430; and Stierle et al., 2007, Biochimie 89(8):1033-1036), two commercially available liposomes, were used. To date, chitosan has been used for the delivery of shRNA encoding plasmids targeting the MDR1 gene. In this study, nanoparticles were formed by complex coacervation (Yang et al., 2009, J Huazhong Univ Sci Technolog Med Sci. April; 29(2):239-42). The maximum mRNA reduction reported in the study was 52.6% with a time dependent reversal of paclitaxel chemoresistance of up to 61.3%. No report to date has described the use of chitosan for the delivery of anti-P-gp siRNA.

The composition described herein can be used either alone or in combination with other anti-cancer compound such as Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon α-2a; Interferon α-2b; Interferon α-n1; Interferon α-n3; Interferon β-Ia; Interferon γ-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; or Zorubicin Hydrochloride.

Other anti-cancer drugs include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; caiphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunornicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide. modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1;

squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Anti-cancer supplementary potentiating compounds include: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and multiple drug resistance reducing compounds such as Cremaphor EL.

Other compounds which are useful in combination therapy for the purpose of the invention include the anti-proliferation compound, Piritrexim Isethionate; the antiprostatic hypertrophy compound, Sitogluside; the benign prostatic hyperplasia therapy compound, Tamsulosin Hydrochloride; the prostate growth inhibitor, Pentomone; radioactive compounds such as Fibrinogen I 125, Fludeoxyglucose F 18, Fluorodopa F 18, Insulin I 125, Insulin I 131, Iobenguane I 123, Iodipamide Sodium I 131, Iodoantipyrine I 131, Iodocholesterol I 131, Iodohippurate Sodium I 123, Iodohippurate Sodium I 125, Iodohippurate Sodium I 131, Iodopyracet I 125, Iodopyracet I 131, Iofetamine Hydrochloride I 123, Iomethin I 125, Iomethin I 131, Iothalamate Sodium I 125, Iothalamate Sodium I 131, Iotyrosine I 131, Liothyronine I 125, Liothyronine I 131, Merisoprol Acetate Hg 197, Merisoprol Acetate Hg 203, Merisoprol Hg 197, Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium Tc 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131, Triolein I 125 and Triolein I 131.

As used herein, "treatment" and "treating" include preventing, inhibiting, and alleviating diabetes mellitus and related conditions and symptoms. The treatment may be carried out by administering a therapeutically effective amount of the composition described herein. In other instances, the treatment may be carried out by concurrently administering a therapeutically effective amount of a combination of insulin and the composition described herein. In still other instances, the treatment may involve concurrently administering a therapeutically effective amount of a combination of a hypoglycemic compound and the composition described herein when the diabetes mellitus and related conditions to be treated is type II diabetes, insulin resistance, hyperinsulinemia, diabetes-induced hypertension, obesity, or damage to blood vessels, eyes, kidneys, nerves, autonomic nervous system, skin, connective tissue, or immune system.

Examples of chitosan containing chemical modification are: chitosan-based compounds having: (i) specific or non-specific cell targeting moieties that can be covalently attached to chitin and/or chitosan, or ionically or hydrophobically adhered to a chitosan-based compound complexed with a nucleic acid or an oligonucleotide, and (ii) various derivatives or modifications of chitin and chitosan which serve to alter their physical, chemical, or physiological properties. Examples of such modified chitosan are chitosan-based compounds having specific or non-specific targeting ligands, membrane permeabilization agents, subcellular localization components, endosomolytic (lytic) agents, nuclear localization signals, colloidal stabilization agents, agents to promote long circulation half-lives in blood, and chemical derivatives such as salts, O-acetylated and N-acetylated derivatives. Some sites for chemical modification of chitosan include: $C_2(NH-CO-CH_3$ or $NH_2)$, $C_3(OH)$, or $C_6(CH_2OH)$.

The compositions described herein are suitable drug delivery systems with effective controlled release properties. The present compositions can be administered with any known combination therapy, such as the co-administration of a suitable delivery reagent such as, but not limited to, Mirus Transit TKO® lipophilic reagent, Lipofectin®, Lipofectamine™, Cellfectin®, polycations (e.g., polylysine) or liposomes.

Concurrent administration" and "concurrently administering" as used herein includes administering a composition as described herein and insulin and/or a hypoglycemic compound in admixture, such as, for example, in a pharmaceutical composition, or as separate formulation, such as, for example, separate pharmaceutical compositions administered consecutively, simultaneously, or at different times.

Suitable hypoglycemic compounds include, for example, metformin, acarbose, acetohexamide, glimepiride, tolazamide, glipizide, glyburide, tolbutamide, chlorpropamide, thiazolidinediones, alpha glucosidase inhibitors, biguanindine derivatives, and troglitazone, and a mixture thereof.

Administration of the composition described herein can be a parenteral administration which includes subcutaneous, intramuscular, intradermal, intramammary, intravenous, and other administrative methods known in the art.

The present invention will be more readily understood by referring to the following examples.

EXAMPLE I

Reparation of Chitosan/dsODN or siRNA Based Nanoparticles Formulations

Ultrapure chitosan samples were produced using quality controlled manufacturing processes eliminate contaminants including proteins, bacterial endotoxins, toxic metals, inorganic and organic impurities. All chitosans had less than 50 EU/g of bacterial endotoxins. Chitosan were selected having a 92% and 80% of degree of deacetylation (Table 1). These chitosans were produced by heterogeneous deacetylation resulting in a block rather than random distribution of acetyl groups. Chitosans were chemically degraded using nitrous acid as described previously (Lavertu et al., 2006, Biomaterials, 27:4815-4824; Lavertu et al., 2003, J Pharmaceutical and Biomedical Analysis, 32:1149-1158) to obtain specific molecular weights of 10 kDa, 40 kDa and 80 kDa, the former at both DDAs of 92% and 80% and the latter at 80% DDA (Table 1).

TABLE 1

Chitosan degree of deacetylation (DDA), average molecular weight (Mn), poly-dispersity index (PDI)

| Experiment | Chitosan | DDA | Mn (kDa) | Mw | PDI |
|---|---|---|---|---|---|
| RecQL1 | Confocal | Rho-92-10 | 92.7 | 10 | 14 | 1.4 |
| RecQL1 | DLS, ESEM, Protection, Stability Assay, FACS, qPCR | 92-10 | 91.7 | 7.1 | 10.08 | 1.427 |
|  |  | 80-40 | 82.5 | 38.37 | 53.4 | 1.392 |
|  |  | 80-10 | 84.4 | 10.82 | 14.525 | 1.343 |
| DDP-IV | Enzymatic test | 92-10 | 92 | 7.46 | 9.32 | 1.25 |
|  |  | 80-10 | 80 | 12.40 | 22.41 | 1.80 |
|  |  | 80-80 | 80.0 | 93.8 | 187.6 | 2.0 |
| ApoB DDP-IV | Protection Assay, FACS, qPCR, in vivo | 92-10 | 92.2 | 8.501 | 12.645 | 1.494 |
|  |  | 80-80 | 80.8 | 71.535 | 118.03 | 1.65 |
|  |  | 80-10 | 84.4 | 10.820 | 14.525 | 1.343 |
| ApoB DDP-IV | Confocal | Rho-92-10 | 92.7 | 10 | 14 | 1.4 |
| ApoB DDP-IV | Stability Assay, DLS, ESEM | 92-10 | 91.7 | 7.1 | 10.08 | 1.427 |
|  |  | 80-80 | 80.0 | 93.8 | 187.6 | 2.0 |
|  |  | 80-10 | 80 | 12.40 | 22.41 | 1.80 |
|  |  | 80-10 | 84.4 | 10.820 | 14.525 | 1.343 |
|  |  | 80-40-5 | 82.5 | 38.375 | 53.410 | 1.392 |
|  |  | 92-40-5 | 92.7 | 60.6 | 37.9 | 1.6 |

Small interfering RNAs targeting the DPP-IV gene were purchased from Dharmacon (Thermo scientific, Dharmacon RNAi Technologies, USA). These siRNA sense and antisense strands are synthesized with 2 nucleotides (UU) 3' overhangs. Candidates consisted in a pool of four sequences targeting the DPP-IV sequence (DPP-IV Seq1: CACUCUAACUGAUUACUUA, SEQ ID NO:1; DPP-IV Seq2: UAGCAUAUGCCCAAUUUAA, SEQ ID NO:2; DPP-IV Seq 3: CAAGUUGAGUACCUCCUUA, SEQ ID NO:3; DPP-IV Seq 4: UAUAGUAGCUAGCUUUGAU, SEQ ID NO:4). ApoB targeting siRNA sequence was custom synthesized using the 2-ACE RNA chemistry by Dharmacon (ApoB Seq1: GUCAUCACACUGAAUACCAAU, (antisense strands are synthesized with 2 nucleotides (AC) 3' overhangs), SEQ ID NO:5; ApoB Seq 2 (sense): 5' CUC UCA CAU ACA AUU GAA AdTdT 3', SEQ ID NO:7; ApoB seq 2 (antisense) 5' UUU CAA UUG UAU GUG AGA GUUoUoU 3' (oU-oU)=2'-O-methyl-uridine overhangs, SEQ ID NO:6; ApoB Seq3 (sense): GGAAUCuuAuAuuuGAUCcA*A, SEQ ID NO:8; ApoB Seq3 (antisense): uuGGAUcAAAuAuAAGAuUCc*c*U, SEQ ID NO:9; 2'O-Methyl modified nucleotides are in lower case and phosphorothioate linkages are represented by asterisks). These sequences were published by Soutschek, et al. (2004, Nature, 432:173-178), Zimmermann et al. (2006, Nature, 441:111-114) and Strapps et al. (2010, Nucleic Acids Research, Vol. 38, No. 14).

RecQL1 targeting siRNA sequence was custom synthesized using the 2-ACE RNA chemistry by Dharmacon (Seq1: 5'-GUUCAGACCACUUCAGCUUdTdT-3', SEQ ID NO:10). This sequence was published by Futami et al. (2008, Cancer Sci, 99:71-80; 2008, Cancer Sci, 99:1227-1236). MDR1 targeting sequences were purchased presynthetised from Dharmacon and are available through their catalogue under the product number: M-003868-02-0010. Candidates consisted of four siRNA targeting the MDR1 sequence: Seq 1 (sense): 5' GCUGAUCUAUGCAUCUUAUUU 3', SEQ ID NO:11; Seq 1 (antisense) 5'AUAAGAUGCAUAGAUCAGCUU 3'; SEQ ID NO:12; Seq 2 (sense): 5'GACCAUAAAUGUAAGGUUUUU 3', SEQ ID NO:13; Seq 2 (Antisense): 5' AAACCUUACAUUUAUGGUCUU 3', SEQ ID NO:14; Seq 3 (sense): 5' GAAACUGCCUCAUAAAUUUUU 3', SEQ ID NO:15; Seq 3 (Antisense): AAAUUUAUGAGGCAGUUUCUU 3', SEQ ID NO:16; Seq 4 (sense): 5'UCGAGUCACUGCCUAAUAAUU3', SEQ ID NO:17; Seq 4 (Antisense): 5'UUAUUAGGCAGUGACUCGAUU 3', SEQ ID NO:18.

dsODN sequences were synthesized using the phosphoramidite chemistry, (Integrated DNA Technologies, Inc) and used for, nanoparticle stability and nuclease protection assays. For flow cytometry analysis, 6-carboxyfluorescein (6FAM) 5' labeled dsODN were used (Integrated DNA technologies, USA).

The rationale of dsODN use for physico-chemical characterization of chitosan nanoparticles presented herein is their siRNA mimicking properties. These mimicking properties are due to similarities at the structural level (double stranded structure, length (21 mers) and nucleotide over hangs) between siRNA and dsODN. Additionally, charge densities are similar between siRNA and dsODN due to identical phosphate residue number/spacing on their back bone. Differences between siRNA and dsODN lie in the substitution of uracil to thymine (U→T) in the dsODN sequences, and in the deoxyribosilation of dsODN sugar back bone. The dsODN sequences were synthesized using the phosphoramidite chemistry, (Integrated DNA Technologies, Inc) and used for size and zeta potential determination, nanoparticles stability and nuclease protection assays. For confocal microscopy, and flow cytometry analysis, 6-carboxyfluorescein (6FAM) 5' labeled dsODN were used (Integrated DNA technologies, USA).

Chitosans with specific Mn and DDA were dissolved over night on a rotary mixer at 0.5% (w/v) in hydrochloric acid using a glucosamine: HCl ratio of 1:1 at a final concentration of 5 mg/mL. Sterile filtered solutions were then diluted with deionized water to obtain the desired ratio (N:P) of amine (chitosan deacetylated groups) to phosphate (dsODNs or siRNA nucleic acids). Nanopartides (92-10-5, 92-150-5, 80-40-5, 80-10-10, 80-10-5, 80-200-5 and 80-80-5) were then prepared by rapid mixing (pippeting) of 100 μL of diluted chitosan solution to 100 μL of dsODN or siRNA at a concentration of 0.05 μg/μL respectively; a concentration of 0.33 μg/μL dsODN was used for stability and nuclease protection assays whereas a concentration of 0.1 μg/μL was used for DLS and ESEM. Nanoparticles were incubated for 30 minutes at room temperature prior to use.

EXAMPLE II

Transfection Experiments

For in vitro transfection, High Glucose-Dulbecco's Modified Eagle's Media (DMEM-HG) was prepared with 0.976 g/L of MES and 0.84 g/L of sodium bicarbonate ($NaHCO_3$)

at pH 6.5. Transfection media without fetal bovine serum (FBS) was equilibrated overnight at 37° C. in a 5% $CO_2$ incubator and pH adjustment to a 6.5 value at 37° C. was performed using sterile HCl (1N) just before transfection. For siRNA transfection performed in a 96 well plate, chitosan/siRNA nanoparticles were prepared as described above, 30 minutes before use. A 100 µl siRNA solution at a concentration of 0.05 µg/µl (3,704 nM) was used for siRNA complexation with chitosan at a 1:1 ratio (v/v). Following complexation, siRNA concentration becomes 0.025 µg/µl (1,852 nM) and nanoparticles were incubated in a ghost plate containing DMEM-HG media, at a final concentration of 0.00135 µg/µl equivalent to 100 nM per well (10 pmol/well) of siRNA. For dsODN transfection performed in a 24 well plate, chitosan/dsODN nanoparticles were prepared as described above, 30 minutes before use. A 100 µl dsODN solution at a concentration of 0.05 µg/µl (3,717 nM) was used for dsODN complexation with chitosan at a 1:1 ratio (v/v). Following complexation, siRNA concentration becomes 0.025 µg/µl (1,858 nM) and nanoparticles were incubated in a ghost plate containing DMEM-HG media, at a final concentration of 0.00135 µg/µl equivalent to 600 nM per well (60 pmol/well) of dsODN. The slight difference in molecular weight between dsODN used for FACS and siRNA is due to the 6FAM labelling of dsODN. Plates containing nanoparticles were equilibrated for 10 minutes at 37° C., 5% $CO_2$. Medium over cells was aspirated and replenished with either 500 µl (24 well plates) or 100 µl per well (96 well plate) of the equilibrated transfection medium at pH 6.5 containing dsODN or siRNA based nanoparticles at a final concentration of 100 nM/well. FBS was added four hours following transfection, to a final concentration of 10% per well. Cells were incubated with chitosan/siRNA nanoparticles until analysis at 24 hours post-transfection. DharmaFECT™ was used as a positive control and both untreated cells and uncomplexed siRNA treated cells were used as negative controls.

The commercially available liposome, DharmaFECT™ (Dharmacon RNAi Technologies, Lafayette, Colo., USA), was used as a positive control for transfection efficiency in all tested cell lines. DharmaFECT™/dsODN (flow cytometry and confocal microscopy) or DharmaFECT™/siRNA (qPCR) lipoplexes (1:2 [w/v] ratio) were prepared following the manufacturer's protocol.

The in vitro transfections involved HEK293, HepG2 (ApoB and DPP-IV), HT-29 (DPP-IV), Caco-2 (DPP-IV), Raw264.7 (ApoB), A549, LS174T and the AsPC1 cell lines, purchased from American Type Cell Culture (ATCC, Manassas, Va.). The MCF7-MDR cell line was a gift from Dr Hamid Morjani (Pads, France). Cells were cultured in minimal essential medium (HepG2), McCoys (HT-29), Dulbecco minimum essential media high glucose (HEK293 and RAW264.7) with 1.85 g/L (HEK293) or 1.5 g/l (RAW264.7) of sodium bicarbonate, (LS174T), F12K (A549), RPMI-1640 (MCF-7 MDR) and RPMI-1640 (AsPC1), and supplemented with 10% FBS (Cedarlane Laboratories, Burlington, ON) at 37° C. and 5% $CO_2$. HepG2 cells were supplemented with 8% FBS. For transfection, cells were plated in 96-well or 24-well culture plates (Corning, N.Y., USA) so to obtain ~50% to ~70% of confluence the day of the transfection.

EXAMPLE III

RNA Extractions and Gene Expression Analysis

Total RNA extraction was performed using the Nucleo-Spin® RNA XS kit from Machery-Nagel. Cells lysis was performed by adding 100 µl RA1 lysis buffer supplemented with 2 µl TCEP and *Streptomyces griseus* chitosanase into each well (Alameh et al., 2010, Int J Nanomedecine, 5:473-481). DNAse treatment of sample was performed when sample were incubated with RA3 buffer before elution. RNA quantification and quality (integrity) assessment were performed using the Agilent Bioanalyzer 2100. RNA Integrity Number (RIN) equal to 7.5 was considered as an acceptance threshold for qPCR analysis.

Reverse transcription of total RNA was performed using the first strand cDNA transcriptor kit (Roche, Laval, Calif.). A total of 0.5-1 µg of RNA/sample was used for the reverse transcription reaction using oligodT primers according to the manufacturer protocol. Gene quantification of chitosan/siRNA treated cells was performed using the ABI PRISM® 7900HT Sequence Detection System. All reactions were run in triplicate and the average values of Cts were used for quantification. Gene expression level was determined using assays with the Universal Probe Library® (UPL) from Roche™. On the other hand, gene expression level for endogenous controls (TBP, HPRT) was determined using the pre-validated TaqMan® gene expression assays. The relative quantification of target genes was determined using the ΔΔCT method. Briefly, the Ct (threshold cycle) values of target genes were normalized to an endogenous control gene (Endogenous control) ($\Delta CT=Ct_{target}-Ct_{endoC}$) and compared with a calibrator: $\Delta\Delta CT=\Delta Ct_{Sample}-\Delta Ct_{Calibrator}$. Relative expression (RQ) was calculated using the Sequence Detection System (SDS) 2.2.2 software (Applied Biosystems) and the formula is $RQ=2^{-\Delta\Delta CT}$.

EXAMPLE IV

Nanoparticles Analysis

Size of chitosan/dsODN and chitosan/siRNA complexes was determined by dynamic light scattering at an angle of 137° at 25° C. using a Malvern Zetasizer Nano ZS®. Samples were measured in triplicates using refractive index and viscosity of pure water in calculations. The zeta potential was measured in triplicates as well using laser Doppler velocimetry at 25° C. using the same instrument and the dielectric constant of water for calculation. For the size determination, reported as the intensity averaged diameter, 50 µl of chitosan was mixed with 50 µl of dsODN or siRNA then completed to 500 µl using 10 mM NaCl. For zeta measurement, nanoparticles were diluted 1:2 using 500 µl of 10 mM NaCl. All formulations of chitosan/dsODN nanoparticles were in the range of 45-156 nm, as measured by DLS. Chitosan/siRNA nanoparticles had mean diameters in the range of 55-105 nm as measured by DLS when complexed to siRNA sequence 1 (SEQ ID NO:5) and 2 (SEQ ID NO:6 and SEQ ID NO:7) (Table 2). For siRNA sequence 3 (SEQ ID NO:8 and SEQ ID NO:9), fully modified, chitosan-siRNA nanoparticles had mean diameters in the range of 104-130 nm (Table 2). No statistical differences in nanoparticle size were observed between dsODN and un-modified siRNA-ApoB (sequence 1; SEQ ID NO:5) and moderately modified siRNA-ApoB complexed to chitosan (sequence 2; SEQ ID NO:6 and SEQ ID NO:7). However, fully modified siRNA sequence yielded larger nanoparticles when complexed to the different chitosans. Chitosan/dsODN and chitosan/siRNA nanoparticles showed higher size values with increasing Mn. No statistically significant differences were observed when comparing DDAs for these specific formulations. As expected, the excess chitosan in all formulations resulted in positively charged nanoparticles as shown by zeta potentials in Table 2, wherein DLS permitted the determination of size and zeta potential, whereas ESEM measured size only.

TABLE 2

Mean size - by intensity - and zeta potential, with standard deviation, of nanoparticles formed with with siRNA-RecQL1 or siRNA-MDR1 in chitosan formulations: 80-10-5, 80-10-10, 80-40-5, 80-200-5, 92-10-5, 92-150; and siRNA-DPP-IV, ODN-ApoB or siRNA-ApoB in chitosan formulations: 80-10-5, 80-10-10, 80-40-5 80-80-5, 92-10-5, 92-40-5.

| Sample | Chitosan | Size (nm) | Zeta potential (mV) | ESEM (nm) |
|---|---|---|---|---|
| MDR1 | 80-10-5 | 70 ± 2 | 12 ± 3 | 62 ± 9 |
| | 80-200-5 | 156 ± 35 | 18 ± 3 | 131 ± 5 |
| | 92-10-5 | 71 ± 15 | 15 ± 2 | 64 ± 8 |
| | 92-150-5 | 140 ± 49 | 17 ± 5 | 123 ± 6 |
| RecQL1 | 80-10-10 | 91 ± 7 | 18 ± 2 | 73 ± 9 |
| | 80-40-5 | 86 ± 9 | 18 ± 1 | 97 ± 12 |
| | 92-10-5 | 63 ± 8 | 23 ± 1 | 54 ± 6 |
| DPP-IV (pool of siRNA seq 1 to seq 4) | 80-10-10 | 81 ± 5 | 16 ± 2 | 70-90 |
| | 80-80-5 | 111 ± 12 | 20 ± 2 | 60-100 |
| | 92-10-5 | 71 ± 7 | 18 ± 2 | 50-90 |
| ApoB (ODN mimics siRNA ApoB seq 1) (mimics of SEQ ID NO: 5) | 80-10-10 | 64 ± 6 | 19 ± 2 | 67 ± 7 |
| | 80-80-5 | 100 ± 12 | 16 ± 1 | 75 ± 13 |
| | 92-10-5 | 45 ± 4 | 21 ± 2 | 66 ± 5 |
| ApoB (siRNA seq 1) (SEQ ID NO: 5) | 80-10-5 | 80 ± 7 | 27 ± 2 | 62 ± 5 |
| | 80-40-5 | 105 ± 6 | 24 ± 5 | 90 ± 7 |
| | 92-10-5 | 55 ± 3 | 28 ± 2 | 60 ± 3 |
| | 92-40-5 | 69 ± 4 | 23 ± 5 | 65 ± 14 |
| ApoB (siRNA seq 2) (SEQ ID NO: 6 and SEQ ID NO: 7) | 80-10-5 | 90 ± 4 | 26 ± 4 | 70 ± 8 |
| | 80-40-5 | 89 ± 6 | 24 ± 5 | 76 ± 7 |
| | 92-10-5 | 57 ± 3 | 26 ± 4 | 54 ± 6 |
| | 92-40-5 | 67 ± 2 | 24 ± 5 | 59 ± 9 |
| ApoB (siRNA seq 3) (SEQ ID NO: 8 and SEQ ID NO: 9) | 80-10-5 | 139 ± 7 | 19 ± 3 | 89 ± 7 |
| | 80-40-5 | 130 ± 2 | 25 ± 2 | 100 ± 9 |
| | 92-10-5 | 105 ± 3 | 22 ± 5 | 78 ± 5 |
| | 92-40-5 | 104 ± 4 | 27 ± 3 | 80 ± 6 |

Nanoparticles formed as described above were imaged using an environmental scanning electron microscope (ESEM, Quanta 200 FEG, FEI Company Hillsboro, Oreg., USA). Following nanoparticle formation, TNCs were sprayed on silicon water substrate, and then sputter-coated with gold (Agar Manual Sputter Coater, Marivac Inc.) as described previously (Lavertu et al., 2003, J Pharm Biomed Anal, 32:1149-1158). Observations were performed at 20 kV in the high vacuum mode of the ESEM microscope. The average particle size (+/− standard deviation) was determined by measuring the diameter of more than 150 particles from at least 6 different fields for each fraction using the microscope XT Docu software (XT Docu, FEI Co). The robustness of size determination was analyzed by comparison of ESEM image analysis size determination to DLS size data.

The results show nanoparticles of spherical shape (FIGS. 1A, 1B, 2A and 2B) with mean diameters ranging between 45-156 nm depending on the chitosan formulation used (Table 2, ESEM). Results obtained with specific formulations described herein are consistent with dynamic light scattering results (Table 2), thereby indicating the robustness of the composition and method described herein. Furthermore, the nanoparticles formed yield reproducible sizes below 200 nm allowing for avoidance of renal clearance thus improving in vivo transfection efficiency and increasing circulating nanoparticles half-life.

Figure 3A:
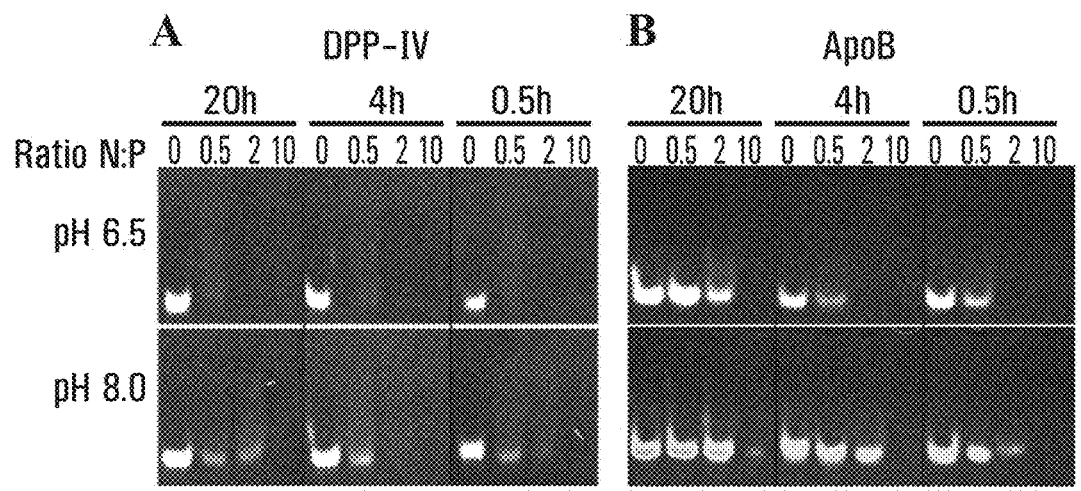
FIG. 3A illustrates a photographic representation of a polyacrylamide gel electrophoresis of chitosan/dsODN nanoparticles possessing various N:P ratios incubated at different pH values and during different time periods. Chitosan 92-10 complexed with (A) dsODN-DPP-IV and (B) dsODN-ApoB and incubated for 0.5 h, 4 h and 20 h in pH6.5 (MES) and pH 8 (TAE) is shown.
Figure 3B:
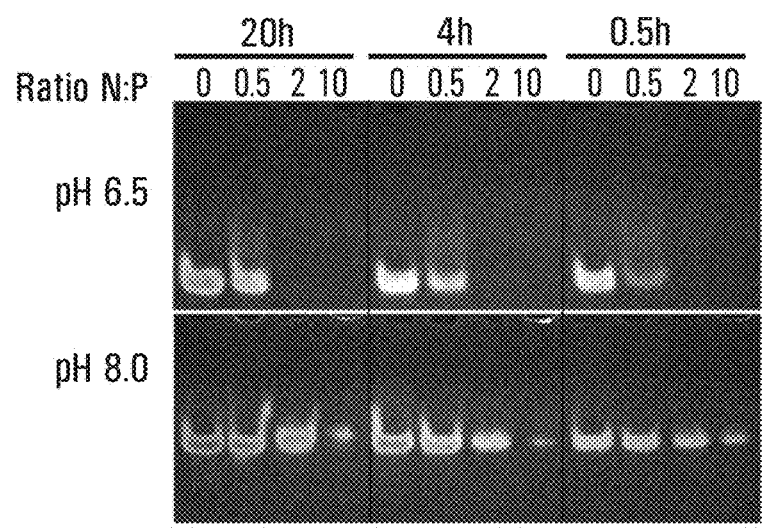
FIG. 3B illustrates a polyacrylamide gel electrophoresis of chitosan/dsODN nanoparticles possessing various N:P ratios incubated at different pH and during different time periods. Chitosan 92-10 complexed with dsODN-RecQL1 and incubated for 0.5 h, 4 h and 20 h in pH6.5 (MES) and pH 8 (TAE). If nanoparticles are not stable in the above-mentioned conditions, siRNA mimicking dsODN are released and migrate in the gel.
Figure 4A:
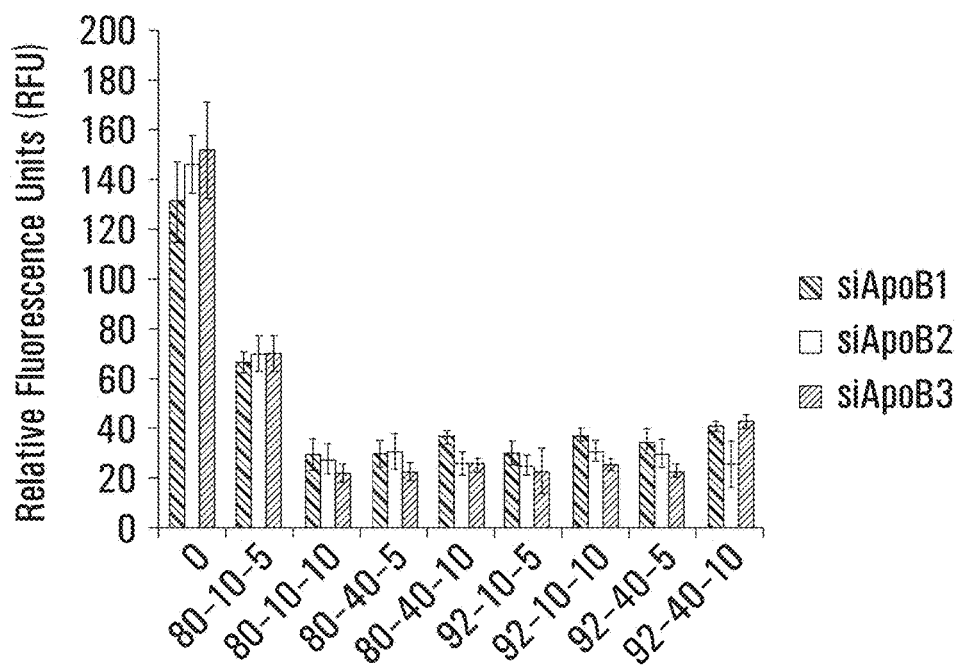
FIG. 4A illustrates histograms of chitosan/siRNA nanoparticle stability at a pH of 6.5, chitosan formulations at different DDA and MW were complexed to three different anti-ApoB siRNA sequences (siApoB1, siApoB2 and siApoB3) at N:P ratios of 5 and 10 and incubated for 20 hours, and following nanoparticle formation Ribogreen™, an RNA intercalating dye used for nucleic acid quantitation, was added to each sample to measure the uncomplexed RNA fraction so that high fluorescence values represent particle disassembly and instability.
Figure 5:
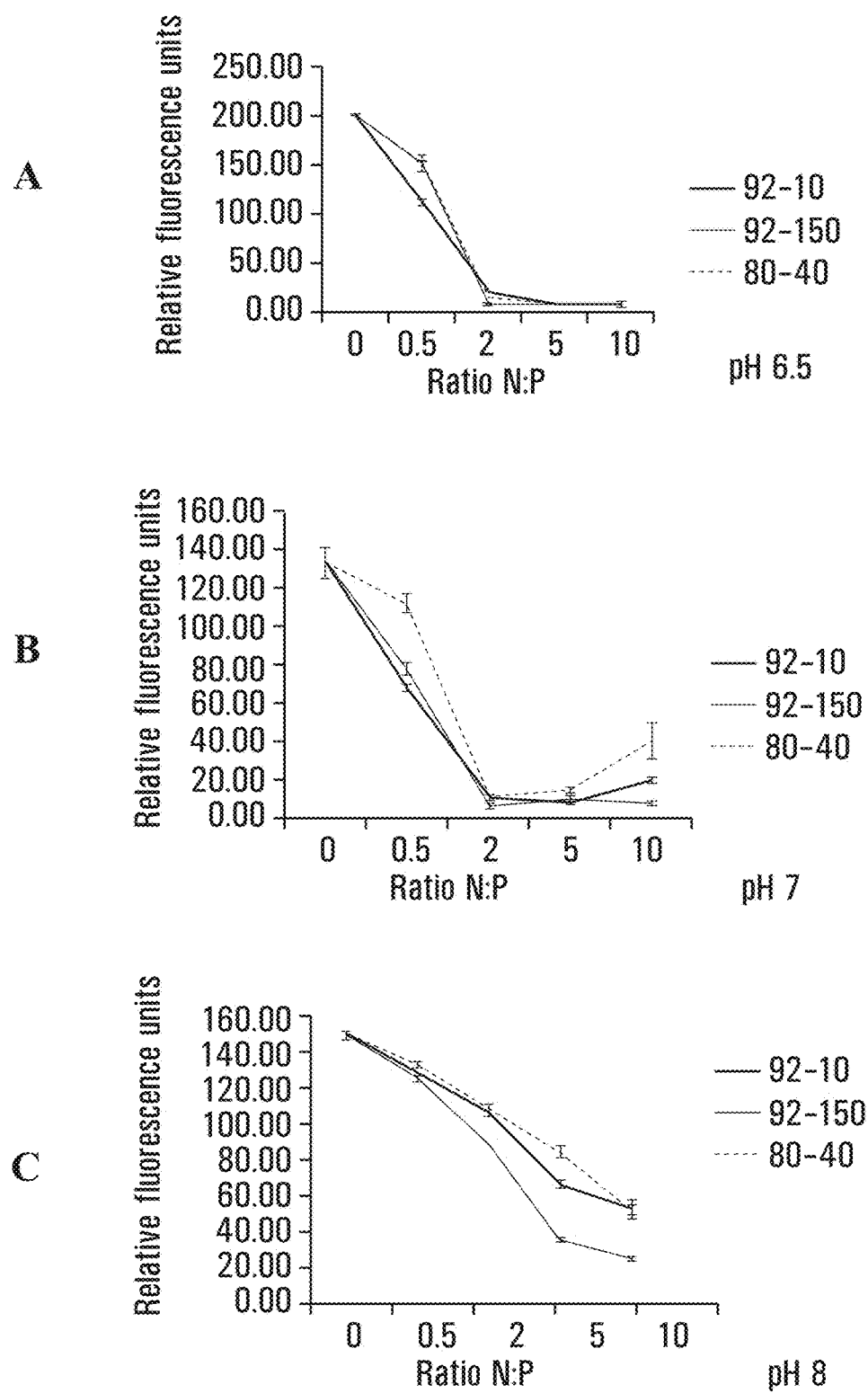
FIG. 5 illustrates the effect of DDA, MW and N:P ratio on nanoparticle stability at different pH where low fluorescence indicates particle stability. Chitosan with various DDA, MW was complexed to anti-MDR1 siRNA at different N:P ratio to form nanoparticles. The latter were incubated at different pH and siRNA release was measured using the Ribogreen™ assay.

Formation and stability of chitosan/dsODN nanoparticles and chitosan/siRNA nanoparticles were tested for up to 20 hours at pH 6.5 and 8 using different methods. Chitosan/dsODN nanoparticles were formed and were stable up to 20 hours at an N:P ratios above 2 at slightly acidic pH (pH 6.5) (FIGS. 3A and 3B). At 4 hours following nanoparticle formation, no detectable dsODN were observed at N:P ratio of 1 (pH 6.5) and higher, whereas complete dsODN release was observed for the same N:P ratio at pH 8. Longer exposure time, 20 h, resulted in dsODN release at N:P ratio of 2 for ApoB dsODN while higher N:P ratio (N:P 10) was able to maintain nanoparticle stability. At pH values of 8, and for the same N:P ratio of 10, partial dsODN release was observed. The specific chitosan formulations described herein assured nanoparticle stability for a minimum period of 20 h at N:P ratio above 2 (N:P>2). Chitosan/siRNA stability was evaluated using the Ribogreen Assay™, a fluorescence based assay, to quantitate the released siRNA following complex destabilization. The results show that chitosan/siRNA nanoparticle with an N:P ratio of 5 and 10 were stable for up to 20 hours at pH 6.5. Chitosan 80-10-5 showed the least stability when compared to other formulations. Increasing the N:P ratio for chitosan 80-10 resulted in an improvement of nanoparticle stability. Except for chitosan 80-10, increasing the N:P ratio above five did not result in an increase of nanoparticle stability as demonstrated by the data (FIGS. 4A and 5). Thus, at lower N:P ratios nanoparticles were unstable and the complexation efficiency was not optimal. At a neutral pH, nanoparticles were stable at N:P ratios between 2 and 5. At a more basic pH of 8, nanoparticles were unstable with a clear requirement to higher N:P ratios and higher molecular weight for increased stability.

Figure 4B:
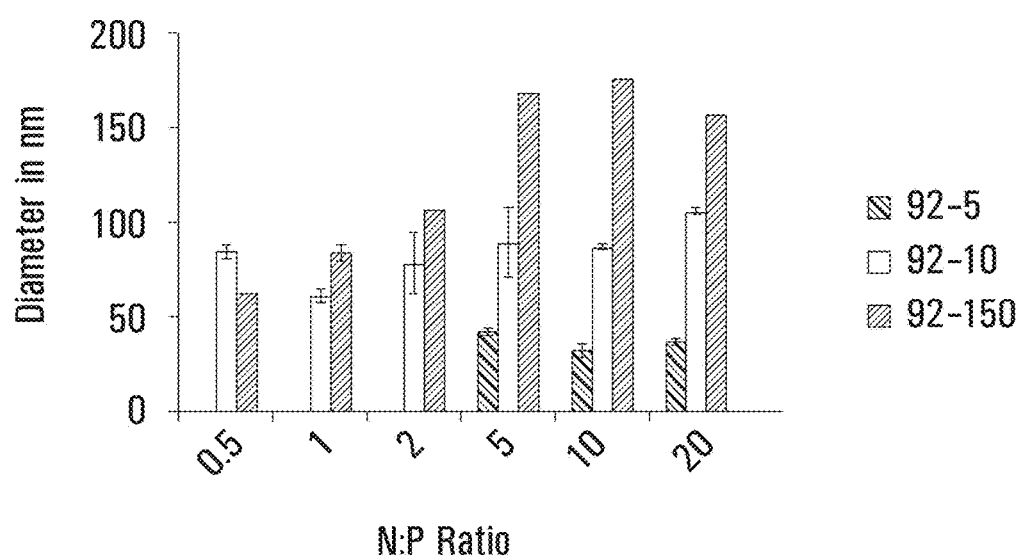
FIG. 4B illustrates a histogram demonstrating the influence of MW on nanoparticle size, chitosan at a DDA of 92% and different MW was complexed to anti-RecQL1 siRNA at different N:P ratio.
Figure 4C:
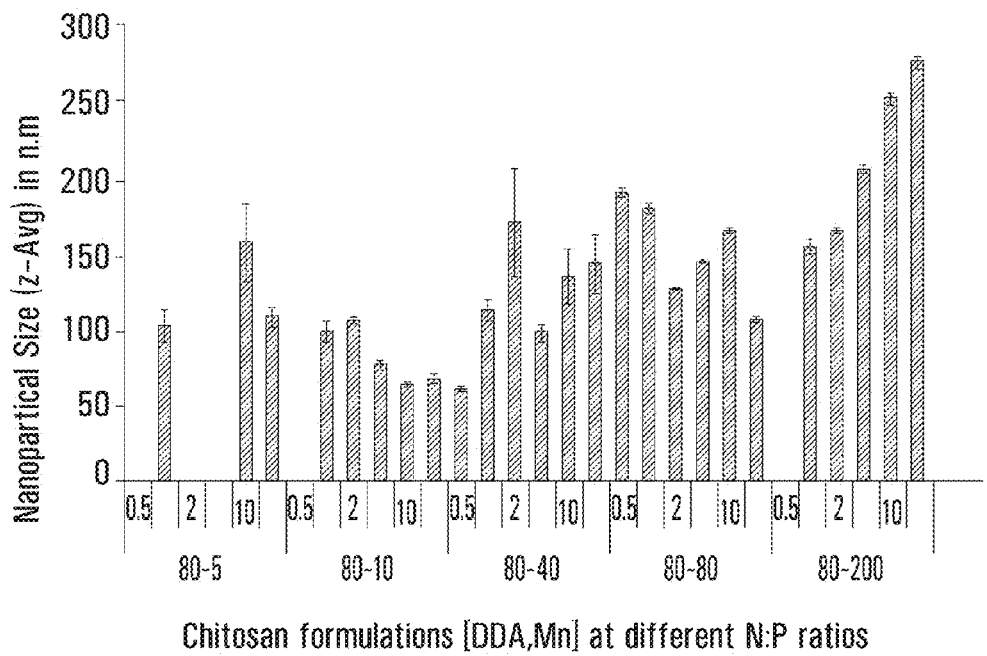
FIG. 4C illustrates a histogram demonstrating the influence of MW on nanoparticle size, chitosan at a DDA of 80% and different MW was complexed to anti-RecQL1 siRNA at different N:P ratio.
Figure 4D:
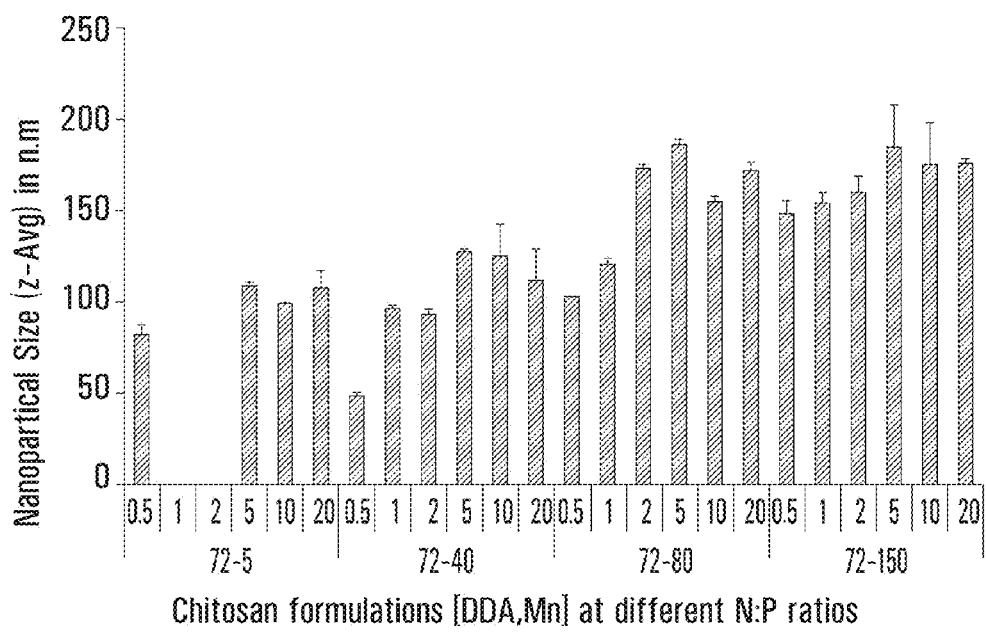
FIG. 4D illustrates a histogram demonstrating the influence of MW on nanoparticle size. Chitosan at a DDA of 72% and different MW was complexed to anti-RecQL1 siRNA at different N:P ratio.

The effect of chitosan parameters (DDA, MW and N:P ratio) was studied using for example anti-RecQL1 siRNA. A clear effect of the molecular weight is apparent with increased nanoparticle size when increasing chitosan MW (FIGS. 4B, 4C and 4D). The DDA had a very slight effect on nanoparticle size. The N:P ratio seem to have a impact on nanoparticle size with higher nanoparticle size at increasing N:P.

Figure 4E:
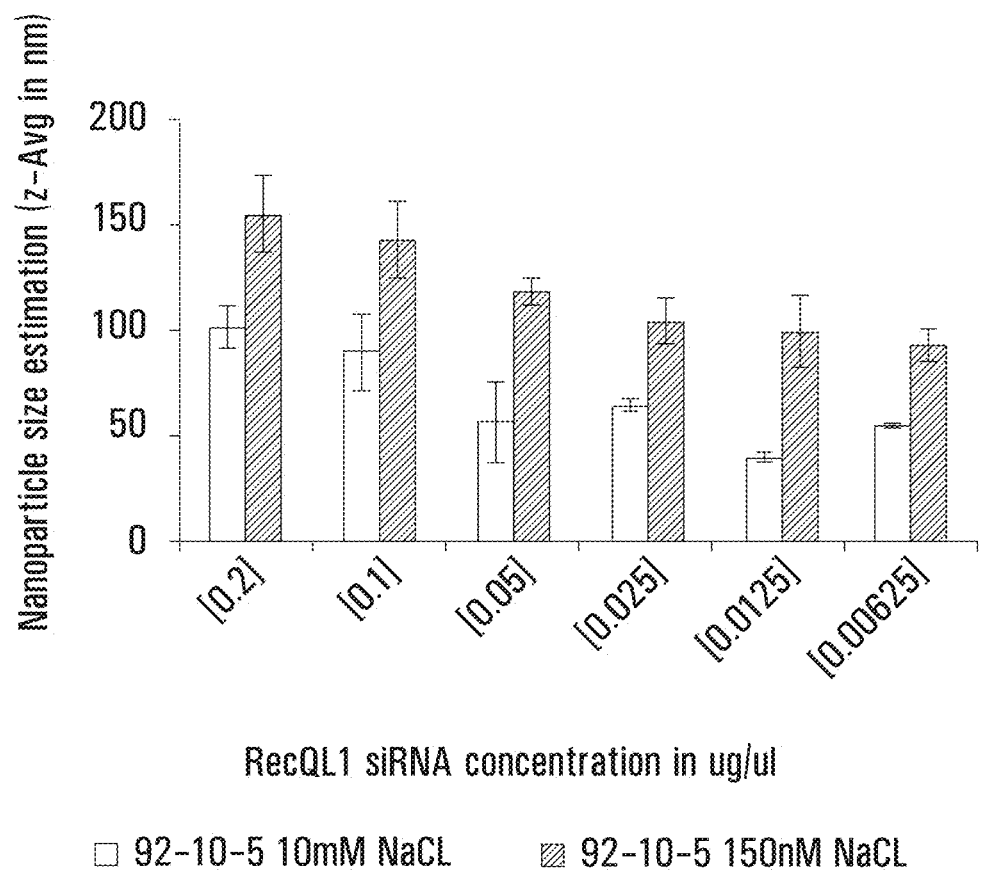
FIG. 4E illustrates a histogram demonstrating the effect of RecQL1 siRNA concentration on nanoparticle size, and the effect of salt on nanoparticle size as measured by dynamic light scattering, chitosan with a DDA of 92%, a Molecular weight of 10 at an N:P ratio of 5 was complexed to increasing concentrations of anti-RecQL1 siRNA.

The effect of siRNA concentration on nanoparticle size was studied. Our results show increased nanoparticle size with increased siRNA concentrations (FIG. 4E).

Figure 6A:
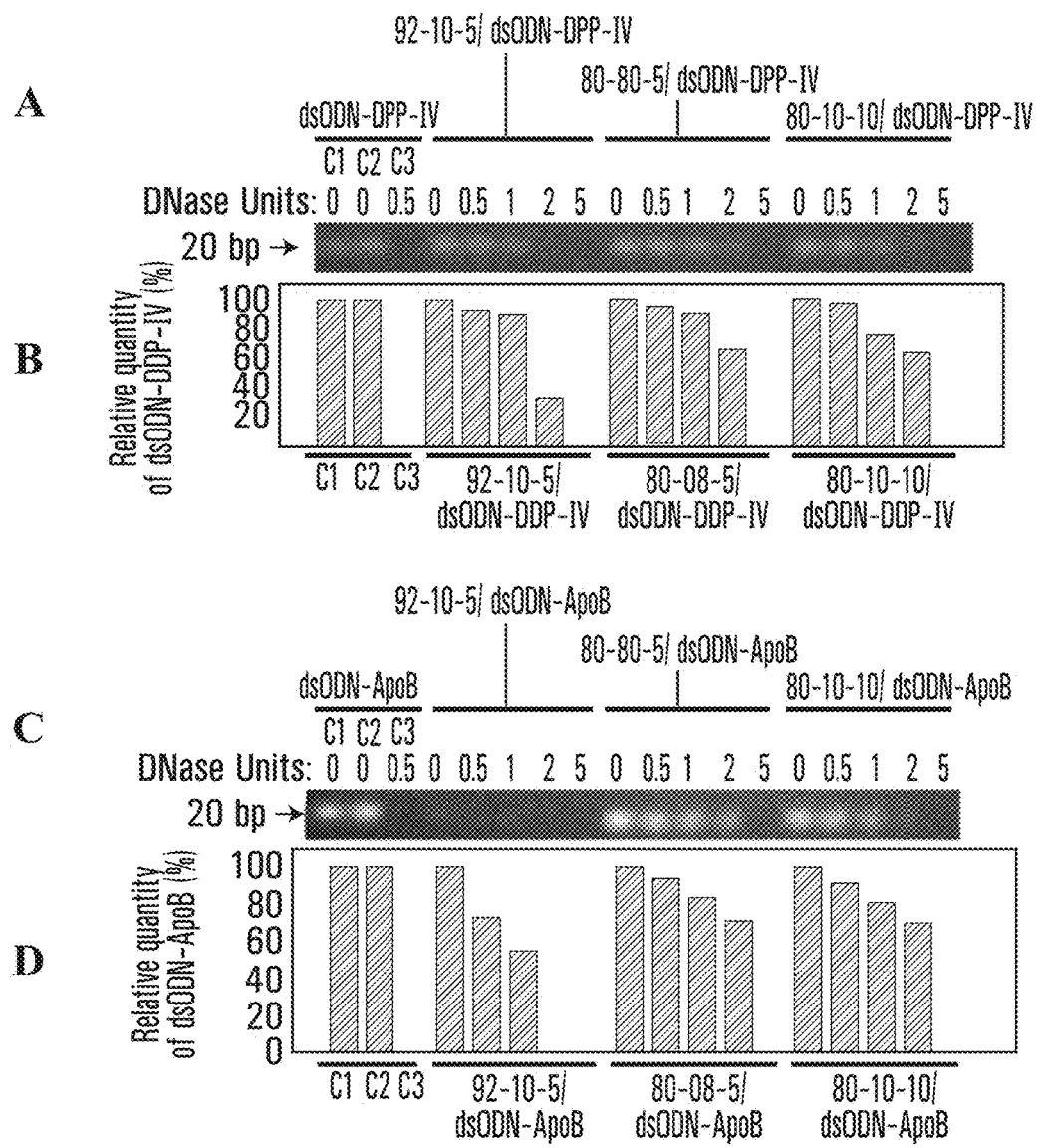
FIG. 6A illustrates results of nuclease protection assays of chitosan/dsODN nanoparticles, (A) chitosan (92-10-5 or 80-10-10) complexed with dsODN-DPP-IV, (B) dsODN-DPP-IV remaining after the DNAse I digestion, (C) chitosan (92-10-5 or 80-10-10) complexed with dsODN-ApoB, (D) dsODN-ApoB remaining after the DNAse I digestion, all digestions were assessed using the signal intensity of the treated samples with the control. (i.e. 0U DNAse I=100% intensity)
Figure 6B:
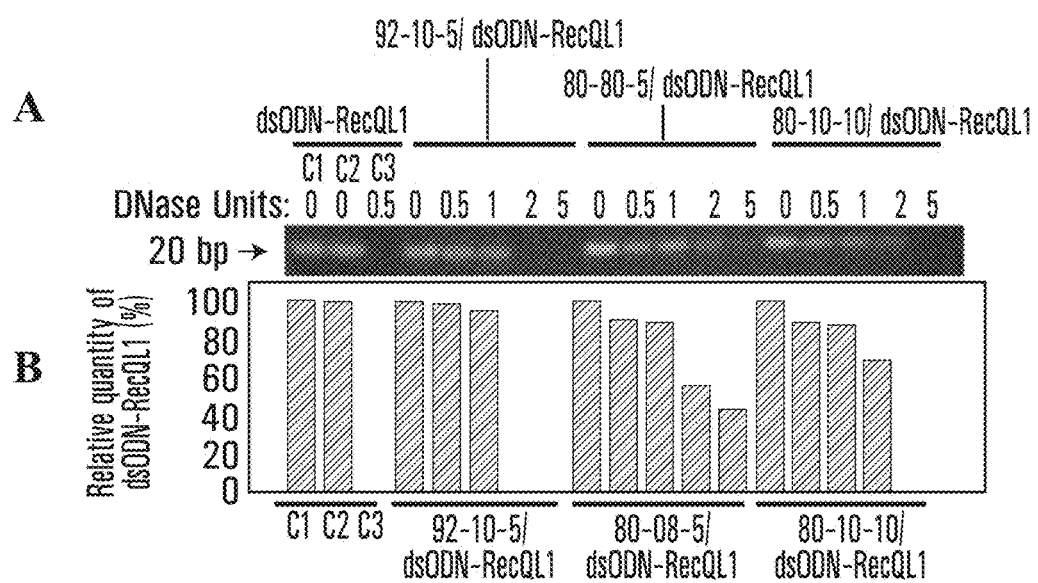
FIG. 6B illustrates nuclease protection assays results of chitosan/dsODN nanoparticles: (A) chitosan (92-10-5, 80-40-5 or 80-10-10) complexed with dsODN-RecQL1, and (B) dsODN-RecQL1 remaining after the DNAse I digestion, all digestions were assessed using the signal intensity of the treated samples with the control. (i.e. 0U DNAse I=100% intensity).

The ability of chitosan to protect dsODN sequences at low N:P ratios was assessed using a DNAse I protection assay. Nanoparticles of chitosan/dsODN (6 µl) were incubated in a buffer containing (pH 6.5) 20 mM MES, 1 mM MgCl$_2$ and a concentration of 0, 0.5, 1, 2, 5 or 10 units of DNAse I. Samples were incubated for 30 min at 37° C. The reaction was stopped by adding 2 µl of EDTA (50 mM) then heated at 72° C. for 15 min. Samples were then assessed by gel electrophoresis. Results demonstrate the ability of the formulations to protect siRNA mimicking double stranded oligonucleotide (FIGS. 6A and 6B). All digestions were assessed using the signal intensity of the treated samples with the control (i.e. 0U DNAse I=100% intensity). The protection is considerable and accounts for approximately 70% of complexes when using 1 unit of DNAse I/µg of DNA whereas the negative control is completely digested when 0.5 unit of DNAse I per µg of DNA is used. The protection remains efficient when increasing DNAse I concentration to 5 units per µg of DNA.

Figure 9:
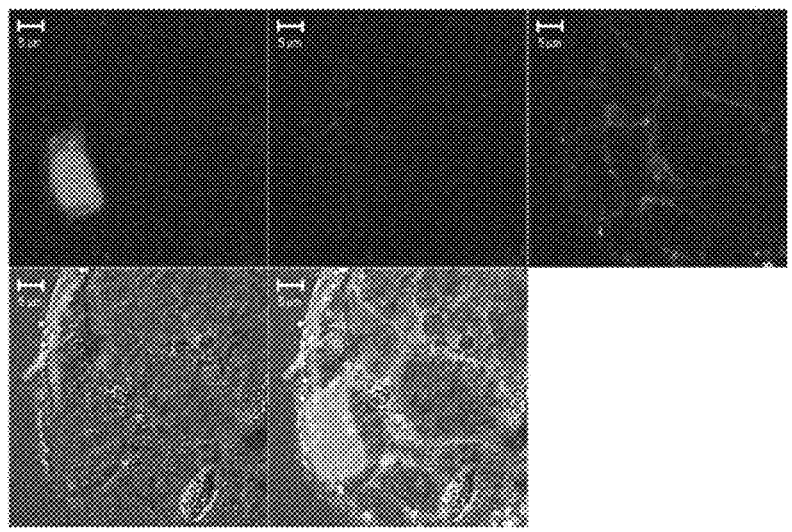
FIG. 9 illustrates confocal imaging of chitosan/siRNA nanoparticle uptake 24 hours post-transfection. LS174T cell lines transfected with chitosan/siRNA-RecQL1 nanoparticles. Images were taken 24 hours post transfection. Chitosan 92-10 (DDA, Mn) was labeled with rhodamine (red) and siRNA were 5' labeled with 6FAM (green). Chitosan 92-10 was complexed to siRNA-RecQL1 at an N:P ratio of 5. Cell membranes were stained prior to imaging with CellMask™ (blue). Images shown represent each separate channels with siRNA in green, chitosan in red, membrane in blue, transmission DIC in grey and the merge images shown on the bottom left quadrant.
Figure 10:
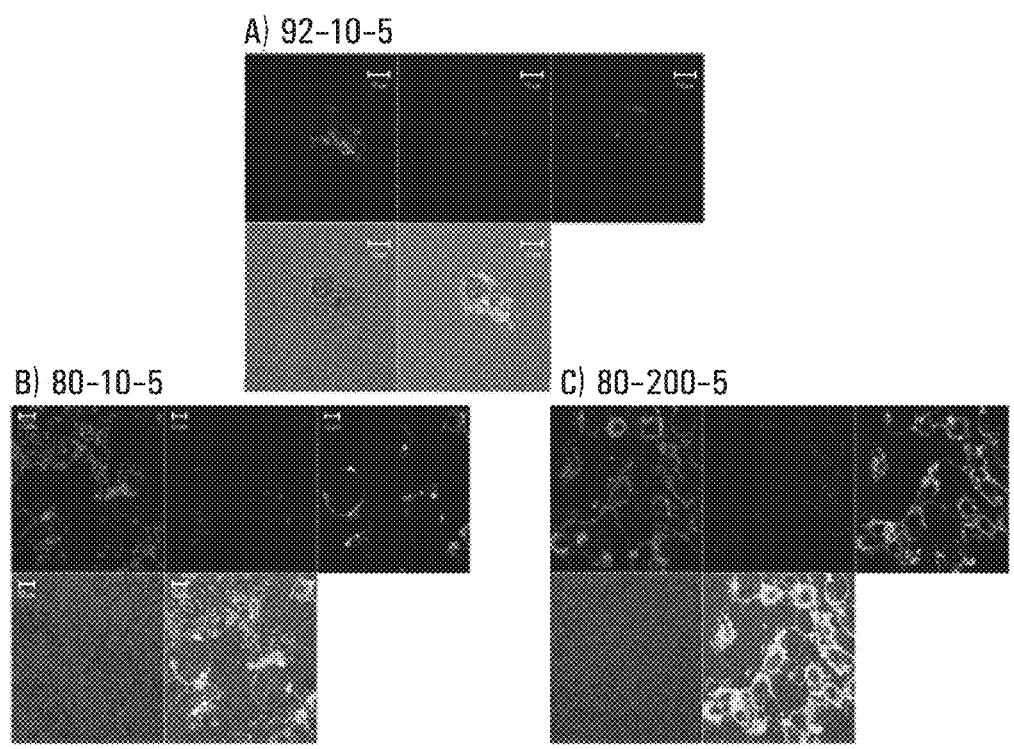
FIG. 10 illustrates confocal imaging of chitosan/siRNA nanoparticle uptake 24 hours post-transfection. MCF-7 MDR cell line transfected with chitosan/siRNA-MDR1 nanoparticles. Images were taken 24 hours post transfection. Chitosan 92-10 (DDA, Mn) was labeled with rhodamine (red) and siRNA were 5' labeled Cy3 (green). Chitosan 92-10 (A) chitosan 80-10 (B) and chitosan 80-200 (C) were complexed to siRNA-cy3 at an N:P ratio of 5. Cell membranes were stained prior to imaging with CellMask™ (blue). Images shown represent each separate channel with siRNA in green, chitosan in red, membrane in blue, transmission DIC in grey and the merge images shown on the bottom left quadrant.

Cell uptake of RecQL1, DPP-IV and ApoB dsODN nanoparticles at different DDA, Mn and N:P ratio was evaluated using FACS analysis of fluorescein labeled dsODN following chitosanase treatment of transfected cells thus reducing any possible bias associated with membrane bound nanoparticles as previously described (Alameh et al., 2010, Int J Nanomedicine, 5:473-481). Interestingly, results obtained with dsODN/chitosan nanoparticles indicate the cell line dependency of efficient uptake. The cell line dependency of chitosan nanoparticles uptake was associated with different endocytic pathways in previous work (Bishop, 1997, Rev Med Virol, 7:199-209; Huang et al., 2002, Pharm Res, 19:1488-1494). FACS results show that in general, cell uptake using these dsODN revealed no differences between formulations (FIGS. 7A and 7B). The uptake efficiency using compositions presented herein ranged from 80% to 98% for RecQL1 (LS174T, A549 and AsPC1 cell lines), from 55% to 80% for ApoB (in HEK293, HepG2 and RAW264.7 cell lines). The uptake efficiency of the DPP-IV dsODN nanocomplexes in HepG2 cell line ranged from 73% to 99% with no statistical differences between the different formulations (92-10-5, 80-10-10 and 80-80-5). Uptake efficiency using chitosan/dsODN nanoparticles achieved levels comparable to or higher than the commercially used lipoplex (DharmaFECT™) with similar relative variation between cells type (FIGS. 7A and 7B). Furthermore, these results are in accordance with confocal microscopy data (FIGS. 8 to 10), described below, where images show a cellular distribution of chitosan and dsODN for all cell lines indicating a qualitative correlation to FACS quantitative data.

Confocal microscopy was used in order to assess particle uptake and internalization into the different cell lines described herein (LS174T, MCF-7 MDR, HEK293, HepG2, Caco-2 and RAW264.7). Chitosan was labeled using rhodamine whereas RecQL1-siRNA, DDP-IV-dsODN and ApoB-dsODN were labeled using fluorescein. For MCF-7 MDR nanoparticle assessment, a Cy3 labeled siRNA was used. Following the labeling process, nanoparticles were formed by mixing 1:1 volume of chitosan-rhodamine and siRNA mimicking dsODN using the procedure described above. Results suggest that formulations described in the present description were efficiently internalized into cells with a maximum release of siRNA or dsODN 24 hours post transfection. The enclosed results indicate the lack of colocalisation at 24 hrs between siRNA or dsODN and chitosan demonstrating that complete release of the siRNA or dsODN cargo was achieved 24 h post transfection. Furthermore, the diffuse staining pattern of siRNA or dsODN seen in most transfected cells is representative of complexes that have escaped endocytic vesicles (FIGS. 8 to 10), consistent with previous live cell imaging work using chitosan-plasmid DNA nanoparticles (Thibault et al., 2010, Mol Ther, 18:1787-1795). Time course studies showed that particle internalization starts within an hour post transfection with a slow release dynamics to reach a maximum 24 hours post transfection.

The above described results show the capability of the formulation described in the present description to transfect and efficiently deliver different dsODN and siRNA into multiple cell lines (FIGS. 8 to 11).

EXAMPLE V

Ex Vivo siRNA Delivery and Gene Expression Inhibition

Figure 11A:
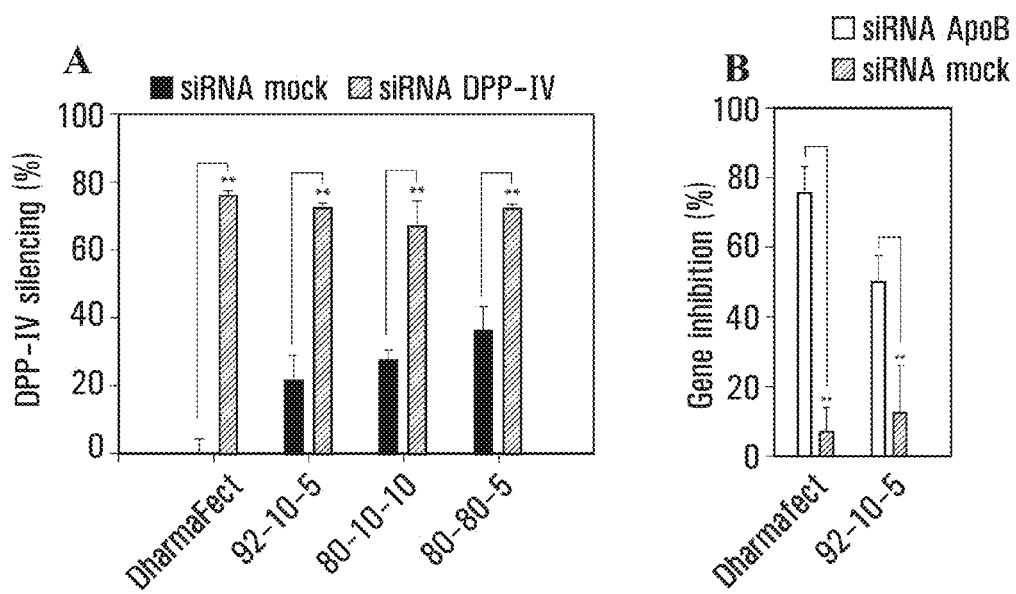
FIG. 11A illustrates histograms of real-time PCR (qPCR) analysis of the inhibition DPP-IV and ApoB gene expression in specific cell lines, HepG2 cells were transfected with: (A) chitosan (92-10-5, 80-80-5 and 80-10-10/siRNA-DPP-IV); (B) chitosan (92-10-5/siRNA-ApoB) nanoparticles, the inhibition percentage was obtained by comparing the transfected and non-transfected cells, using the $\Delta\Delta CT$ method.
Figure 11B:
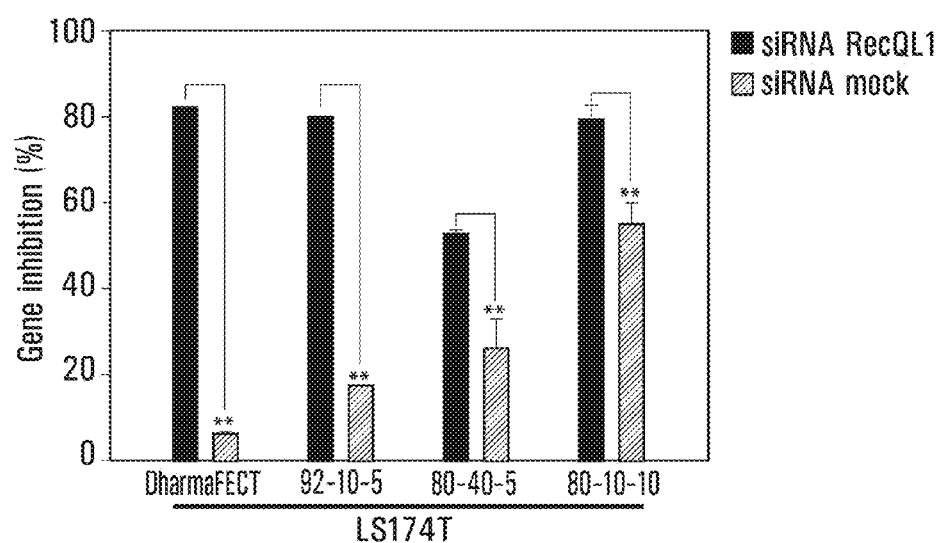
FIG. 11B illustrates a histogram showing Real-time PCR (qPCR) analysis of the inhibition RecQL1 gene expression in specific cell lines, LS174T cells were transfected with chitosan (92-10-5, 80-40-5 and 80-10-10/siRNA-RecQL1), the inhibition percentage was obtained by comparing the transfected and non-transfected cells, using the $\Delta\Delta CT$ method.

Chitosan specific formulations (92-10-5, 80-40-5, 80-10-10 and 80-80-5) were assessed for the siRNA delivery and subsequent inhibition of gene expression (RecQL1 mRNAs, DPP-IV, or ApoB mRNAs) in different cell lines. Results show that RecQL1, DPP-IV and ApoB coding mRNAs were down-regulated more than two fold when measured by quantitative real time PCR (FIGS. 11A and 11B). These results demonstrate that the formulation described herein can achieve levels of gene silencing comparable to the commercial liposome DhamaFECT™ without any apparent cytotoxicity as observed using the alamar blue assay.

More specifically, regarding inhibiton of RecQL1 mRNAs in LS174T cells, chitosan 92-10-5 showed a high level of silencing (~80%), similar to the current gold standard commercial formulation (~80%), used in the present description as a positive control. Formulations 80-40-5 and 80-10-10 also induced significant silencing but to a lower degree than 92-10-5 and also with an increase of non-specific mock silencing, especially for formulation 80-10-10 (FIG. 11B). The results disclosed herein clearly reveal the effectiveness of the described chitosan-based formulations to efficiently deliver siRNA and knock down specific genes at N:P ratios far below (N:P=5) those used previously by others (N:P>20). In general, all of our low N:P ratio chitosan formulations reached high level of gene silencing supporting the FACS data (FIG. 7B).

Figure 12:
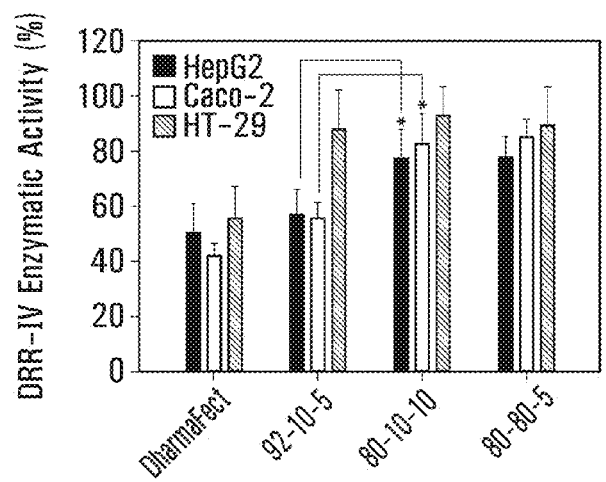
FIG. 12 illustrates a histogram showing DPP-IV enzymatic activity in three different DPP-IV expressing cell lines. DPP-IV inhibition percentages were determined in comparison with siRNA-mock transfected cells. Values are expressed as mean±s.d.; n=4/group. *p<0.05, ** p<0.01.

It was found that 70% gene silencing at the messenger RNA level (mRNA) of DPP-IV or ApoB mRNAs, can be achieved using the specific formulation consisting of chitosan 92-10 with an N:P ratio of 5 (FIG. 11A). However the 70% inhibition at the messenger level is translated to a reduction of 50% of the enzymatic activity of DPP-IV (FIG. 12). This inhibition at the enzymatic level is comparable to that achieved when using the commercial lipoplex DharmaFECT™.

EXAMPLE VI

In Vivo Efficiency Analysis of Chitosan/siRNA Nanoparticles

The in vivo efficiency of siRNA-ApoB nanoparticles was evaluated in a C57BL/6 mouse model. For each treatment modality, four animals (n=4 except for the Dα where n=2 and the C1 group where n=3) were injected with 1 mg kg$^{-1}$ of siRNA targeting the ApoB gene. The 1 mg kg$^{-1}$ siRNAs targeting the ApoB gene were complexed to low molecular weight chitosan (LMW-CS) in a final volume of 0.2 ml (injected volume For example, for a 39 g mouse a 39 μg siRNA—calculated for a dose of 1 mgkg$^{-1}$—was administered following complexation of a siRNA volume of 78 μl at 0.5 μg/μl (37,037 nM) at a 1:1 ratio of chitosan 92-10-5. The total volume of 156 μl was then administered. The siRNA concentration following complexation becomes 0.25 μg/μl (18,518 nM). Specifically, siRNA targeting the ApoB gene were complexed to chitosan formulation 92-10 (DDA, Mn) at an N:P ratio of 5 (N:P 5). In total, five groups (C1 to C5; n=4/group) were TNC treated at different times following the schedule in Table 3, wherein data for intravenous injections schedule of chitosan/siRNA-ApoB nanoparticles at a dose of 1 mg kg$^{-1}$ anti-ApoB siRNA in various C57BL/6 mice groups (n=4 animal per group) is disclosed. Each day represents the only day in the week where injections were made or euthanasia was performed. All the mice were injected once per week for three weeks with the TNC 92-10-5 (Mn-DDA-N:P), with the exception of 2 mice from the Dα group which were injected with the TNC 92-10-5 just once and euthanized 2 days later, to examine the rapidity of the therapeutic response. With the exception of these 2 mice, all other mice were euthanized within the last week of January 2011. The Dα group served as the positive untreated atherosclerotic control while Dμ was the negative control group that received the normal low fat diet. The Dβ group was the negative control group for the siRNA delivery without chitosan and was injected with uncomplexed naked siRNA. The total number of animals used for this study was 32.

TABLE 3

Animal study schedule Groups

| Day | C1 (n = 3) | C2 (n = 4) | C3 (n = 4) | C4 (n = 4) | C5 (n = 4) | Dα (n = 4) | Dβ (n = 4) | Dμ (n = 4) |
|---|---|---|---|---|---|---|---|---|
| 23/11/10 | | | | Acclimation (All groups) | | | | |
| 30/11/10 | Injection #1 | | | | | | | |
| 07/11/10 | Injection #2 | Injection #1 | | | | | | |
| 14/12/10 | Injection #3 | Injection #2 | Injection #1 | | | | | |
| 21/12/10 | | Injection #3 | Injection #2 | Injection #1 | | | Injection #1 | |
| 28/12/10 | | | Injection #3 | Injection #2 | Injection #1 | | Injection #2 | |
| 04/01/10 | | | | Injection #3 | Injection #2 | | Injection #3 | |
| 11/01/11 | | | | | Injection #3 | | | |
| 18/01/11 | | | | | | Dα – 2day Injection (n = 2) / Dα n = | | |
| 20/01/11 | | | | | | Euthanasia Dα-2 day | | |
| 26/01/11 | Euthanasia (C1, C2, C3) | | | | | | | |
| 27/01/11 | | | | Euthanasia (C4, C5) | | Euthanasia (Dα, Dβ, Dγ) | | |

All animals were acclimatized for two weeks before experimentation as requested by the University of Montreal Animal Ethic Committee (CDEA). Following the two week of acclimatization, high fat chow—D12492—was fed to all treated groups including the Dα positive group (untreated group, n=4) and the Dβ naked siRNA treated group (n=4) until the completion of the study which corresponds to the day where animals were euthanatized (Table 3). The Dμ group (n=4) was fed regular chow—D12450B—and served as the normal negative control (lean group). All treated animals were injected once a week for three weeks (Table 3). All C group animals were injected with 1 mg kg$^{-1}$ of ApoB siRNA using the low N:P chitosan formulation 92-10-5. The last of the 3 weekly injections occurred at 7, 6, 5, 4 and 3 weeks prior to euthanizing groups C1, C2, C3, C4, C5, in order to examine the time course of treatment. Two of the 4 positive control atherosclerotic Dα animals were injected with the above formulation two days prior to euthanasia to examine the onset of treatment, with the other two remaining untreated. The D group was treated with uncomplexed naked ApoBsiRNA at 1 mg kg$^{-1}$ while the normal low fat diet group Dμ was not treated (details in Table 3)

During the experimental schedule, phlebotomy was performed once per two weeks whereas animal weight measurement was performed once per week before TNC injection until the completion of the study. At the end of the experimental schedule and following the sacrifice of all animals (Table 3), organs such as liver and intestine were removed for analysis.

Hematological, biochemical, serological and histological analysis were performed on all animals. For instance, hematological and biochemical analysis of sera were performed by VitaTech, Montreal, Canada. The quantification of ApoB reduction in the sera was performed using an anti-ApoB ELISA whereas the quantification of LDL/VLDL cholesterol was performed using a colorimetric assay. Staining of liver sections was performed using hematoxylin-eosin staining in order to visualize fat vacuole. For the evaluation of immune cells infiltration into the liver, paraffin embedded sections were stained with Safranin-O/fast-green/iron-hematoxylin.

Hematological and biochemical analysis of all animals were performed following serum collection the day of euthanasia. Alanine aminotrasferase (ALT) and aspartate aminotrasferase (AST), two sensitive indicator of liver damage were quantified in treated and untreated animals. A comparison of ALT and ASL plasma levels between the treated group (C5) and the positive control group (Dα) did not show any significant difference indicating an absence of liver toxicity effects of treatment with low N:P chitosan-ApoB siRNA TNCs (Table 4).

Moreover, results show that serum albumin levels were normal both in treated and untreated groups also indicating normal liver function. However, total cholesterol quantification in siRNA-ApoB treated animals showed potentially elevated serum levels similar to the positive control group (Table 4), wherein C5-2 was administered chitosan/siARN-ApoB nanoparticles, whereas Dα-3 is a positive control for atherosclerosis development respectively. Only one animal per group was used for haematological analysis because serum volumes needed are high and require the sacrifice of one animal.

TABLE 4

Haematologic characterization of a treated (C5-2) and untreated (Dα-3) mice.

| Mice (Group-Mice) | C5-2 | Dα-3 |
|---|---|---|
| Albumin (g/L) | 35 | 35 |
| Bilirubin (Total) (μmol/L) | 0.4 | 0.7 |
| Bilirubin (Conjugated) (μmol/L) | 0.1 | 0 |
| ALP (IU/L) | 58 | 55 |

TABLE 4-continued

Haematologic characterization of a treated (C5-2) and untreated (Dα-3) mice.

| Mice (Group-Mice) | C5-2 | Dα-3 |
|---|---|---|
| ALT (IU/L) | 120 | 121 |
| AST (IU/L) | 213 | 222 |
| GGT (IU/L) | 0 | 0 |
| Cholesterol (mg/dL) | 220 | 209 |
| Hemolysis | 1+ | 1+ |
| Icterus | Normal | Normal |
| Lipemia | Normal | Normal |

Taken together these results indicate the safety of the low N:P chitosan based siRNA nanoparticles as they do not induce any liver damage.

Apolipoprotein B plasma concentration levels in µg/ml were assessed using an anti-ApoB commercial ELISA kit (Uscn Life science Inc., China). The determination of ApoB plasma levels varied between 597 µg/mL and 1,433 µg/mL depending on the groups and controls tested. The results obtained show that all treated groups had ApoB plasma levels that were ~35% reduced from the positive atherosclerotic control group Dα to reach levels similar to those of the normal negative control (Dµ) (FIG. 13). The Dα-2 day group showed a similar reduction two days following injection indicating a rapid silencing effect following TNC injection.

ApoB levels were decreased by 35% in animals receiving uncomplexed siRNA (control group; Dβ-1). Although this treatment modality (Dβ-1) was similarly effective in ApoB plasma reduction as TNCs treatment modalities (FIG. 13), it resulted in high inflammatory reactions in the liver (FIG. 16H) thus limiting its dosing to achieve effective and therapeutic silencing/ApoB plasma reduction. Additionally, results show that reductions in ApoB plasma levels for low N:P chitosan-based TNCs was maintained for more than seven weeks after the last injection in the C1 animal group (FIG. 13) without any apparent inflammation or liver toxicity. These results indicate a particularly promising the longevity of TNC treatment and effective controlled release properties.

The comparison between the Dβ-1 and the C1-C5 groups toxicity/inflammatory profiles indicate the advantage of using these specific LMW-TNCs over naked siRNA since no apparent toxicity/inflammation profile was observed (FIG. 16 and Table 4).

The LDL/VLDL cholesterol concentration was determined using a commercial quantitative colorimetric detection kit BioAssay Systems, USA). Results herein show that treated animals demonstrated a reduction in LDL/VLDL of ~20% compared to the positive control (Dα) (FIG. 14). Interestingly, group C5 demonstrated a higher concentration of VLDL/LDL compared to the untreated group despite the observed ApoB reduction (FIG. 13); a reduction comparable to other groups showing concomitant reduction of both ApoB and VLDL/LDL plasma concentration. The comparison between naked siRNA treated animals and TNCs treated animals show a similar reduction in LDL/VLDL cholesterol concentrations in accordance with previous results where ApoB reduction was similar (FIGS. 13 and 14).

Histological analysis of paraffin fixed liver sections stained with hematoxylin-eosin reveal that TNC treated animals had lower cholesterol accumulation compared to the positive control Dα. Liver sections form TNC treated groups, C3 and Dβ, were found to have low levels of accumulated cholesterol similar to the normal negative control group Dµ that was fed the low fat diet. (FIG. 15). On the contrary, the group C4, C5 and Dα2 presented fatty livers similar to the positive control Dα (FIG. 15) whereas C1 and C2 present intermediate fatty livers. All together, results demonstrate that TNCs can prevent excessive cholesterol accumulation in the liver through ApoB inhibition and LDL/VLDL reduction therefore permitting the liver conversion of cholesterol into bile in C1, C2, and C3 groups. The results observed in groups C4 and C5 appear to be due to an excessive accumulation of cholesterol before TNC treatment. These results demonstrate the effectiveness of chitosan based TNCs in the treatment of atherosclerosis.

Histological analysis of paraffin fixed liver sections stained with safranin-O/fast-green/iron-hematoxylin show that chitosan based TNCs reduced the inflammatory reaction compared to naked ApoB siRNA treatment (FIG. 16). Results show that C5 group presented a higher lymphoid cell infiltration rates than the atherogenic control group thus indicating that inflammation was due to chitosan deposition in liver (FIG. 16). However, histological analysis of liver from groups C4, C3, C3 and C1 show a time dependent resorption of inflammation (FIG. 16). Furthermore, the comparison of Dα-2 day and the positive untreated control Dα-3 show that chitosan effects of lymphoid cell infiltration is time dependent (FIGS. 16, F and G). It is estimated that nanoparticles dependent inflammation within several weeks of treatment and is preserved during approximately three weeks until the resorption.

Comparison of FIGS. 15 and 16 allows the assessment of the efficiency of the chitosan based nanoparticles to prevent cholesterol accumulation in the liver without disruption of liver integrity as demonstrated in by the ALT/ASL profiles. Furthermore, the comparison between FIGS. 13 and 14 pinpoint the longevity of the treatment thus confirming our previous observations of chitosan mediated slow release.

Figure 17:
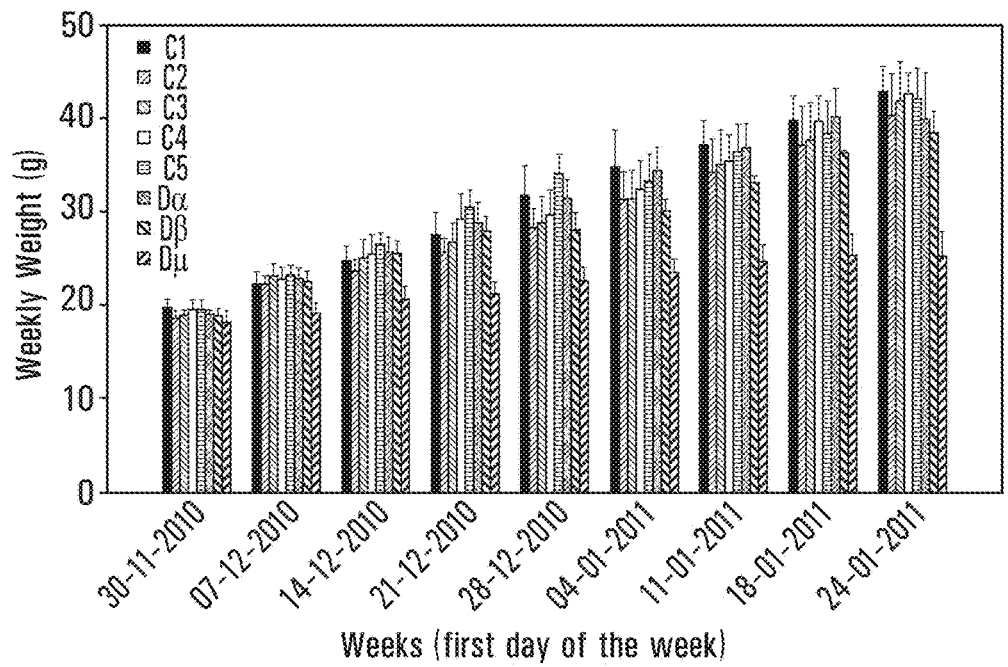
FIG. 17 illustrates a histogram showing the weekly weight (g) measurements of all animal groups. All animals were weighed on the first day of each week, before each chitosan/siRNA administration. Compared to the low fat normal control Dμ, a continual weight gain over 4 weeks was observed for all animals fed with the high fat diet that was essentially unaffected by NTC treatment.
Figure 18:
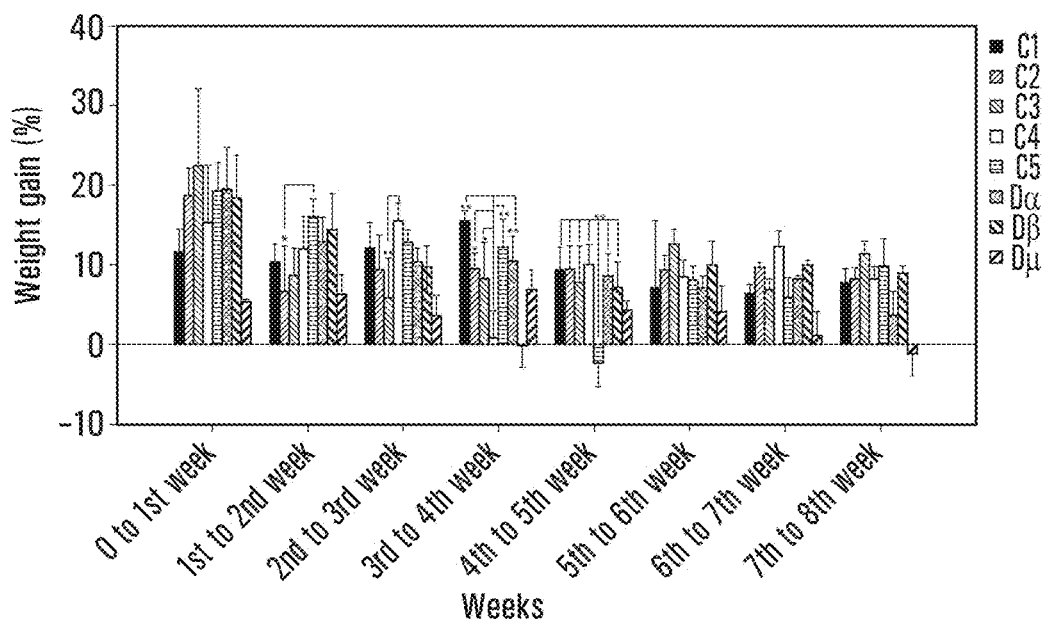
FIG. 18 illustrates a histogram showing the percentage of weight gain per week. All animals were weighed on the first day of each week, before chitosan/siRNA administration. Weight gain consists in the relative difference between the weight of the animal and its recorded weight the previous week $[(t_{n-1}-t_n)/t_{n-1})]$. This figure show immediate weight gain or loss following the first TNC administration.

The effect of treatment on weight gain was assessed by measuring the weight of each animal/group once per week during the present study. Results show that treatment did not affect weight gain (FIG. 17). However, it was noted that weight gain was slowed in the week following first TNC administration. For example, group C4 and C5 received their first injection on the $3^{rd}$ and $4^{th}$ week of investigation, respectively, which caused weight stabilization for group C4 and weight loss for group C5. This effect is also present in groups C2 and C3 on a smaller scale (FIG. 17). In fact, C5's mean weight had an accelerated weight gain (mean weight) compared to all groups from the beginning of the study until its first injection on 28-12-2010. The effect of this injection is observed on 04-01-2011 ($5^{th}$ week) where C5's weight increase rate slowed drastically concordantly with what is observed in FIG. 18.

While the invention has been described in connection with specific embodiments thereof, it will be understood that it is capable of further modifications and this application is intended to cover any variations, uses, or adaptations of the invention, including such departures from the present disclosure as come within known or customary practice within the art to which the invention pertains and as follows in the scope of the appended claims.

What is claimed is:

1. A method for in vivo delivery of an RNAi-inducing nucleic acid molecule in a patient, the method comprising: administering to said patient a composition comprising chitosan and an RNAi-inducing nucleic acid molecule, wherein the RNAi-inducing nucleic acid molecule is a short interfering RNA (siRNA) or a short hairpin RNA (shRNA), wherein the chitosan has a molecular weight (Mn) of 5 kDa to 200 kDa, a degree of deacetylation (DDA) of 80% to 95%, wherein the chitosan amine to nucleic acid phosphate ratio (N:P) is below 20.

2. The method of claim 1, wherein the Mn is of 5 to 15 kDa, the DDA is from 90 to 95% and the N:P ratio is from 2 to 10.

3. The method of claim 1, wherein the Mn is 10 kDa, the DDA is 92% and the N:P ratio is 5.

4. The method of claim 1, wherein the chitosan comprises block distribution of acetyl groups or a chemical modification.

5. The method of claim 1, wherein said chitosan has a polydispersity between 1.0 and 7.0.

6. The method of claim 1, wherein the RNAi-inducing nucleic acid molecule is chemically modified either on the sugar backbone, phosphate backbone and/or the nucleotide base ring.

7. The method of claim 1, wherein said administering is selected from subcutaneous, intramuscular, intradermal, intramammary, intravenous, intraperitoneal, oral and gastrointestinal administration.

8. The method of claim 1, wherein the RNAi-inducing nucleic acid molecule induces RNAi of a gene involved in pathogenesis of type II diabetes, atherosclerosis or cancer.

9. The method of claim 1, wherein the RNAi-inducing nucleic acid molecule induces RNAi of a gene is involved in tumor development, metastasis or the induction of chemoresistance.

10. The method of claim 1, wherein the RNAi-inducing nucleic acid molecule induces RNAi of a gene encoding a glycoregulating protein.

11. The method of claim 10, wherein the glycoregulating protein is an incretin degrading enzyme.

12. The method of claim 11, wherein the incretin degrading enzyme is dipeptydilpeptidase-IV (DPP-IV).

13. The method of claim 1, wherein the RNAi-inducing nucleic acid molecule induces RNAi of a gene encoding an atherogenic protein.

14. The method of claim 13, wherein the atherogenic protein is Apolipoprotein B (ApoB), Apolipoprotein E (ApoE), Apolipoprotein B 100 (ApoB 100), Apolipoprotein B 48 (ApoB 48), Neutrophil gelatinase-associated lipocalin (NGAL), Matrix metalloproteinase-9 (MMP-9), or Cholesteryl ester transfer protein (CETP).

15. The method of claim 1, wherein the RNAi-inducing nucleic acid molecule induces RNAi of a gene encoding a helicase protein, an RNA helicase, P68, DDX5, DDX32, DDX1, Akt, PKB, a member of the ABC transporters, MDR1, MRP, a member of the RAS family of proteins, SRC, HER2, EGFR, Abl, or Raf.

16. The method of claim 15, wherein the helicase protein is a member of the RecQ family of helicases.

17. The method of claim 16, wherein the helicase protein is RecQL1 DNA helicase.

18. The method of claim 1, wherein said subject has or is diagnosed as having diabetes mellitus or a related condition thereof.

19. The method of claim 1, wherein said subject has or is diagnosed as having atherosclerosis or a related condition thereof.

20. The method of claim 1, wherein said subject has or is diagnosed as having cancer or a related condition thereof.

21. The method of claim 1, wherein the Mn is of 5 to 15 kDa.

22. The method of claim 1, wherein the DDA is from 90 to 95%.

23. The method of claim 1, wherein the N:P ratio is from 2 to 10.

24. The method of claim 1, wherein the chitosan and the RNAi-inducing nucleic acid molecule are in the form of a particle having a size below 200 nm.

* * * * *

SEQUENCE LISTING

```
<160> NUMBER OF SEQ ID NOS: 18

<210> SEQ ID NO 1
<211> LENGTH: 21
<212> TYPE: RNA
<213> ORGANISM: Artificial Sequence
<220> FEATURE:
<223> OTHER INFORMATION: DPP-IV sequence Seq1

<400> SEQUENCE: 1
cacucuaacu gauuacuuau u                                              21

<210> SEQ ID NO 2
<211> LENGTH: 21
<212> TYPE: RNA
<213> ORGANISM: Artificial Sequence
<220> FEATURE:
<223> OTHER INFORMATION: DPP-IV sequence Seq2

<400> SEQUENCE: 2
uagcauaugc ccaauuuaau u                                              21

<210> SEQ ID NO 3
<211> LENGTH: 21
<212> TYPE: RNA
<213> ORGANISM: Artificial Sequence
<220> FEATURE:
<223> OTHER INFORMATION: DPP-IV sequence Seq3

<400> SEQUENCE: 3
caaguugagu accuccuuau u                                              21

<210> SEQ ID NO 4
<211> LENGTH: 21
<212> TYPE: RNA
<213> ORGANISM: Artificial Sequence
<220> FEATURE:
<223> OTHER INFORMATION: DPP-IV sequence Seq4

<400> SEQUENCE: 4
uauaguagcu agcuuugauu u                                              21

<210> SEQ ID NO 5
<211> LENGTH: 21
<212> TYPE: RNA
<213> ORGANISM: Artificial Sequence
<220> FEATURE:
<223> OTHER INFORMATION: ApoB sequence Seq1

<400> SEQUENCE: 5
gucaucacac ugaauaccaa u                                              21

<210> SEQ ID NO 6
<211> LENGTH: 23
<212> TYPE: RNA
<213> ORGANISM: Artificial Sequence
<220> FEATURE:
<223> OTHER INFORMATION: ApoB seq 2 (antisense)
<220> FEATURE:
<221> NAME/KEY: modified_base
<222> LOCATION: 21
<223> OTHER INFORMATION: cm
<221> NAME/KEY: modified_base
<222> LOCATION: 22
<223> OTHER INFORMATION: am
<223> OTHER INFORMATION: phosphorothioate linkage between positions
      21-22 and 22-23
```

```
<400> SEQUENCE: 6
auugguauuc agugugauga cac                                              23

<210> SEQ ID NO 7
<211> LENGTH: 21
<212> TYPE: RNA
<213> ORGANISM: Artificial Sequence
<220> FEATURE:
<223> OTHER INFORMATION: ApoB seq 2 (sense)
<223> OTHER INFORMATION: phosphorothioate linkage between position 20
      and 21

<400> SEQUENCE: 7
gucaucacac ugaauaccaa u                                                21

<210> SEQ ID NO 8
<211> LENGTH: 21
<212> TYPE: RNA
<213> ORGANISM: Artificial Sequence
<220> FEATURE:
<223> OTHER INFORMATION: ApoB Seq3 (sense)
<220> FEATURE:
<221> NAME/KEY: modified_base
<222> LOCATION: 19
<223> OTHER INFORMATION: cm
<220> FEATURE:
<221> NAME/KEY: modified_base
<222> LOCATION: 7, 8, 10, 12, 13, 14
<223> OTHER INFORMATION: um
<220> FEATURE:
<223> OTHER INFORMATION: phosphorothioate linkage between position 20
      and 21

<400> SEQUENCE: 8
ggaaucuuau auuugaucca a                                                21

<210> SEQ ID NO 9
<211> LENGTH: 23
<212> TYPE: RNA
<213> ORGANISM: Artificial Sequence
<220> FEATURE:
<223> OTHER INFORMATION: ApoB Seq3 (antisense):
<220> FEATURE:
<221> NAME/KEY: modified_base
<222> LOCATION: 1, 2, 11, 13, 18
<223> OTHER INFORMATION: um
<220> FEATURE:
<221> NAME/KEY: modified_base
<222> 7,    21,    22
<223> OTHER INFORMATION: cm
<220> FEATURE:
<223> OTHER INFORMATION: phosphorothioate linkage between positions
      21-22 and 22-23

<400> SEQUENCE: 9
uuggaucaaa uauaagauuc ccu                                              23

<210> SEQ ID NO 10
<211> LENGTH: 21
<212> TYPE: DNA
<213> ORGANISM: Artificial Sequence
<220> FEATURE:
<223> OTHER INFORMATION: RecQL1 targeting siRNA sequence (Seq1)
<220> FEATURE:

<400> SEQUENCE: 10
guucagacca cuucagcuut t                                                21

<210> SEQ ID NO 11
```

```
<211> LENGTH: 21
<212> TYPE: RNA
<213> ORGANISM: Artificial Sequence
<220> FEATURE:
<223> OTHER INFORMATION: MDR1 Seq 1 (sense)

<400> SEQUENCE: 11
gcugaucuau gcaucuuauu u                                              21

<210> SEQ ID NO 12
<211> LENGTH: 21
<212> TYPE: RNA
<213> ORGANISM: Artificial Sequence
<220> FEATURE:
<223> OTHER INFORMATION: MDR1 Seq 1 (antisense)

<400> SEQUENCE: 12
auaagaugca uagaucagcu u                                              21

<210> SEQ ID NO 13
<211> LENGTH: 21
<212> TYPE: RNA
<213> ORGANISM: Artificial Sequence
<220> FEATURE:
<223> OTHER INFORMATION: MDR1 Seq 2 (sense)

<400> SEQUENCE: 13
gaccauaaau guaagguuuu u                                              21

<210> SEQ ID NO 14
<211> LENGTH: 21
<212> TYPE: RNA
<213> ORGANISM: Artificial Sequence
<220> FEATURE:
<223> OTHER INFORMATION: MDR1 Seq 2 (antisense)

<400> SEQUENCE: 14
aaaccuuaca uuuauggucu u                                              21

<210> SEQ ID NO 15
<211> LENGTH: 21
<212> TYPE: RNA
<213> ORGANISM: Artificial Sequence
<220> FEATURE:
<223> OTHER INFORMATION: MDR1 Seq 3 (sense)

<400> SEQUENCE: 15
gaaacugccu cauaaauuuu u                                              21

<210> SEQ ID NO 16
<211> LENGTH: 21
<212> TYPE: RNA
<213> ORGANISM: Artificial Sequence
<220> FEATURE:
<223> OTHER INFORMATION: MDR1 Seq 3 (antisense)

<400> SEQUENCE: 16
aaauuuauga ggcaguuucu u                                              21

<210> SEQ ID NO 17
<211> LENGTH: 21
<212> TYPE: RNA
<213> ORGANISM: Artificial Sequence
<220> FEATURE:
<223> OTHER INFORMATION: MDR1 Seq 4 (sense)

<400> SEQUENCE: 17
```

```
ucgagucacu gccuaauaau u                                              21

<210> SEQ ID NO 18
<211> LENGTH: 21
<212> TYPE: RNA
<213> ORGANISM: Artificial Sequence
<220> FEATURE:
<223> OTHER INFORMATION: MDR1 Seq 4 (antisense)

<400> SEQUENCE: 18
uuauuaggca gugacucgau u                                              21
```